(12) United States Patent
Wang et al.

(10) Patent No.: US 7,745,229 B2
(45) Date of Patent: Jun. 29, 2010

(54) CHEMOSELECTIVE FLUORGENIC MOLECULAR LINKERS AND METHODS FOR THEIR PREPARATION AND USE

(75) Inventors: Qian Wang, Columbia, SC (US); Krishnamoorthy Sivakumar, Bangalore (IN)

(73) Assignee: University of South Carolina

( * ) Notice: Subject to any disclaimer, the term of this patent is extended or adjusted under 35 U.S.C. 154(b) by 699 days.

(21) Appl. No.: 11/578,565

(22) PCT Filed: Apr. 15, 2005

(86) PCT No.: PCT/US2005/012966

§ 371 (c)(1), (2), (4) Date: Oct. 16, 2006

(87) PCT Pub. No.: WO2005/103705

PCT Pub. Date: Nov. 3, 2005

(65) Prior Publication Data
US 2007/0224695 A1    Sep. 27, 2007

Related U.S. Application Data

(60) Provisional application No. 60/563,060, filed on Apr. 16, 2004, provisional application No. 60/568,804, filed on May 6, 2004.

(51) Int. Cl.
| G01N 33/533 | (2006.01) |
| C07K 1/10 | (2006.01) |
| C07K 1/13 | (2006.01) |
| C07D 311/04 | (2006.01) |

(52) U.S. Cl. .................. 436/546; 436/56; 436/800; 530/402; 549/200; 552/8

(58) Field of Classification Search ............... None
See application file for complete search history.

(56) References Cited

U.S. PATENT DOCUMENTS

| 3,839,351 A | 10/1974 | Dorlars et al. ........ 260/308 A |
| 7,365,178 B2 * | 4/2008 | Campbell et al. ........ 536/23.1 |
| 2005/0032081 A1 * | 2/2005 | Ju et al. ........ 435/6 |

OTHER PUBLICATIONS

Saxon, E., et al., Science, 287: 2007-10 (2000).
Breinbauer, R. et al., Chembiochem, 4:1147-9 (2003).
Gaietta et al., Science, 296:503-507 (2002).
Lemieux et al., J. Am. Chem. Soc., 125:4708-4709 (2003).
Rostovtsev et al., Angew. Chem., Int. Ed., 41:2596-2599 (2002).
Tornoe et al., J. Org. Chem., 67:3057-3062 (2002).
Wang et al., J. Am. Chem. Soc., 125:3192-3193 (2003).
Speers et al., J. Am. Chem. Soc., 125:4684-4687 (2003).
Seo et al., J. Org. Chem., 68:609-612 (2003).
Lee et al., J. Am. Chem. Soc., 125:9588-9589 (2003).
Link et al., J. Am. Chem. Soc., 125:11164-11165 (2003).
Deiters et al., J. Am. Chem. Soc., 125:11782-11783 (2003).

* cited by examiner

*Primary Examiner*—Shafiqul Haq
(74) *Attorney, Agent, or Firm*—Dority & Manning, P.A.

(57) ABSTRACT

The present invention describes a bioconjugation strategy and compounds that are useful therein in which a fluorescent signal is produced when two molecular or supramolecular entities are linked by chemoselective combination of one linker having an azido or halide substituent group with another linker having a cyano or an alkyne substituent group. A kit is also provided.

40 Claims, 7 Drawing Sheets

CHEMOSELECTIVE FLUORGENIC MOLECULAR LINKERS AND METHODS FOR THEIR PREPARATION AND USE

CROSS REFERENCE TO RELATED PATENTS AND PATENT APPLICATIONS

The present application is the National Stage of International Application No. PCT/US2005/12966 filed Apr. 15, 2005, which was a non-provisional of and claims the benefit of U.S. Provisional Application having the title: Bioconjugation with Fluorogenic Molecular Linkers, that was filed on Apr. 16, 2004, and assigned Ser. No. 60/563,060, and also to U.S. Provisional Patent Application Ser. No. 60/568,804, filed May 6, 2004, each of which are incorporated herein by reference thereto.

BACKGROUND OF THE INVENTION (1) Field of the Invention

The present invention relates to the formation of fluorescent linkages, and more particularly to the formation of chemoselective fluorescent linkages between compounds, including conjugation of biomolecules.

(2) Description of the Related Art

It is often useful to be able to measure the degree of attachment of certain compounds to certain other compounds. This selective binding, or conjugation, is particularly useful in biological assays and diagnostic procedures in which marker compounds selectively bind to target compounds. If the marker compound has properties that can be measured by some sensing method, then its presence can be measured, thereby providing an indirect measurement of the target compound to which it is bound. This technique has been of significant utility in research in the life sciences in methods such as in vivo imaging, drug delivery, biochemical assays, bioengineering, cell-based assay and microarrays, and the like. For general information, see, for example, Saxon, E. et al., *Science,* 287: 2007-10 (2000), and Breinbauer, R. et al., *Chembiochem* 4:1147-9 (2003).

Bioconjugation technology affects almost every discipline of the life sciences, such as drug discovery, proteomics and cell biology. Bioconjugation aims at the linking of two or more molecules (or supramolecules) to form a new complex with the combined properties of its individual components. See Hermanson, G. T. et al., *Bioconjugate Techniques,* Academic Press, San Diego (1996). One important application of bioconjugation is to modify cellular components selectively with signaling probes for proteomics, functional genetics, and cell biology research.

A multistep procedure is commonly employed wherein the cellular entity is first attached with a detectable tag, such as fluorescent dyes or biotin, followed by purification of the ligated product and detection. However, excess prelabled reagents are generally hard to remove from the intracellular environment or from tissues of living organisms, which prohibits the application of a multistep labeling procedure in many situations.

While several bioconjugation techniques are widely used, most of them rely on the reaction between electrophiles and nucleophiles, which can hardly offer truly chemoselective reactions. In addition, the lack of an efficient way to detect and evaluate bioconjugation efficiencies is the big obstacle of many applications. The common way for applying this method of detection is a two-step or three-step procedure. First, the conjugation will introduce the primary labeling reagents, such as biotin and peptide tags. After the purification, the fluorescent secondary reagents will be used to give the detectable signals.

An ideal alternative to present bioconjugation systems would be a chemoselective process that was unaffected by biological components, and which used reagents which, while unbound, did not contribute a significant background signal, but which resulted in a ligated product that provided a strong detectable signal. Very few such systems have been reported.

One system, reported by Gaietta et al., *Science,* 296:503-507 (2002), utilized the synthesis and application of a biarsenical fluorophore which can bind with a short peptide sequence -Cys-Cys-Xaa-Xaa-Cys-Cys- with high affinity, then become strongly fluorescent. Even though the in vivo test provided good results, the method suffers from the high concentration of biarsenical compounds needed to overcome the non-specific finding from other cysteine residues as well as the high toxicity of the biarsenical reagents.

In other work, Lemieux et al., *J. Am. Chem. Soc.,* 125: 4708-4709 (2003), or Saxon et al., *Science,* 287:2007-2010 (2000), report the use of a fluorogenic coumarin-phosphine that is activated by the Staudinger reaction with azides. This yielded a coumarin-phosphine product compound that was unstable to oxidation that can give rise to a high level of false background signals. Also, phosphine is not a bio-friendly reagent. Therefore, such a system would appear to have limited applications in real biomedical situations.

Recent advances in the Cu(I)-catalyzed Huisgen 1,3-dipolar cycloaddition of azides and alkynes has provided promising reactions that appear to afford regioselectivity and almost quantitative transformation under mild conditions. See, e.g., Rostovtsev et al., *Angew. Chem., Int. Ed.,* 41:2596-2599 (2002), or Tornoe et al., *J. Org. Chem.,* 67:3057-3062 (2002). Several groups have used these compounds as a pair of linkers for chemoselective ligations through a Cu(I)-mediated cycloaddition reaction. See, e.g., Wang et al., *J. Am. Chem. Soc,* 125:3192-3193 (2003), or Speers et al., *J. Am. Chem. Soc.,* 125:4684-4687 (2003), or Seo et al., *J. Org. Chem.,* 68:609-612 (2003), or Lee et al., *J. Am. Chem. Soc.,* 125: 9588-9589 (2003), or Link, et al., *J. Am. Chem. Soc.,* 125: 11164-11165 (2003), or Deiters et al., *J. Am. Chem. Soc.,* 125:11782-11783 (2003), or Brienbauer et al., *ChemBioChem,* 4:1147-1149 (2003).

However, the need remains for a bioconjugation method that would have a high chemoselectivity, but which did not affect and was unaffected by biological components, and which used reagents which, while unbound, did not contribute a significant background signal, but which resulted in a ligated product that provided a strong detectable signal.

SUMMARY OF THE INVENTION

Briefly, therefore the present invention is directed to a novel method of forming a linkage complex having a fluorescent signal, the method comprising: contacting a first linkage compound having the structure A-$(Y)_y$—$N_3$, or A-$(Y)_y$—X; with a second linkage compound having the structure E-$(Z)_z$—C≡$CR^E$, or E-$(Z)_z$—C≡N; to form a linkage complex having a fluorescent signal that is different than the fluorescent signal of the first linkage compound and the fluorescent signal of the second linkage compound; where: at least one of A and E is a fluorophore, and any A or E that is not a fluorophore is an organic or inorganic group; X is halo, and when the first linkage compound is A-$(Y)_y$—X, the first linkage compound is contacted with the second linkage compound in the presence of an azide salt of lithium, sodium, or potassium;

$R^E$ is any chemically possible substituent group, y and z are each independently an integer from 0 to 20; and Y and Z are each independently a branched or unbranched alkyl, alkenyl, or alkynyl, which can be substituted or unsubstituted. In certain embodiments, the linkage complex comprises a triazole or a tetrazole.

In another embodiment, the first linkage compound and the second linkage compound can be linked to molecules, diagnostic or therapeutic drugs, or supramolecular structures, such as proteins and cells, or the like, so that conjugation of two such materials can be promoted and/or monitored.

The present invention is also directed to a novel method of detecting the formation of a linkage between a first material and a second material, the method comprising contacting a first linkage compound having the structure $A\text{-}(Y)_y\text{—}N_3$, or $A\text{-}(Y)_y\text{—}X$; with a second linkage compound having the structure $E\text{-}(Z)_z\text{—}C\equiv CR^E$, or $E\text{-}(Z)_z\text{—}C\equiv N$; to form a linkage complex having a fluorescent signal that is different than the fluorescent signal of the first linkage compound and the fluorescent signal of the second linkage compound; where: at least one of A and E is a fluorophore, and any A or E that is not a fluorophore is an organic or inorganic group; X is halo, and when the first linkage compound is $A\text{-}(Y)_y\text{—}X$, the first linkage compound is contacted with the second linkage compound in the presence of an azide salt of lithium, sodium, or potassium; $R^E$ is any chemically possible substituent group, y and z are each independently an integer from 0 to 20; Y and Z are each independently a branched or unbranched alkyl, alkenyl, or alkynyl, which can be substituted or unsubstituted; and measuring the fluorescent signal of the linkage complex.

The present invention is also directed to a novel kit for forming a linkage complex having a fluorescent signal, the kit comprising a first linkage compound having the structure $A\text{-}(Y)_y\text{—}N_3$, or $A\text{-}(Y)_y\text{—}X$; and a second linkage compound having the structure $E\text{-}(Z)_z\text{—}C\equiv CR^E$, or $E\text{-}(Z)_z\text{—}C\equiv N$; where: at least one of A and E is a fluorophore, and any A or E that is not a fluorophore is an organic or inorganic group; X is halo, and when the first linkage compound is $A\text{-}(Y)_y\text{—}X$, the first linkage compound is contacted with the second linkage compound in the presence of an azide salt of lithium, sodium, or potassium; $R^E$ is any chemically possible substituent group, y and z are each independently an integer from 0 to 20; Y and Z are each independently a branched or unbranched alkyl, alkenyl, or alkynyl, which can be substituted or unsubstituted.

Among the several advantages found to be achieved by the present invention, therefore, may be noted the provision of a chemoselective linking method that is easy to use, the provision of such a method that provides a fluorescent signal only upon establishment of the desired linkage, the provision of such a method that can be used under mild, physiologically harmless conditions, the provision of such a method in which the product fluorescent linkage can be readily distinguished from the excess starting reagent, the unbound reagent does not contribute to the background signal in an assay, and the provision of such a method that can be carried out in one reaction step.

DETAILED DESCRIPTION OF THE PREFERRED EMBODIMENTS

In accordance with the present invention, a novel chemoselective conjugation strategy has been discovered that can switch on a fluorescent signal when two molecular or supramolecular entities are linked. This invention is applicable for conjugating two entities, including small molecules (such as drugs, ligands, catalysts, and the like), peptides, proteins, nucleic acids, oligonucleotides, saccharides, viruses, cells, organic polymers, and inorganic polymers (including nanoparticles), and permitting the measurement of the conjugation by fast and easy measurement of the fluorescent emission.

Figure 1:
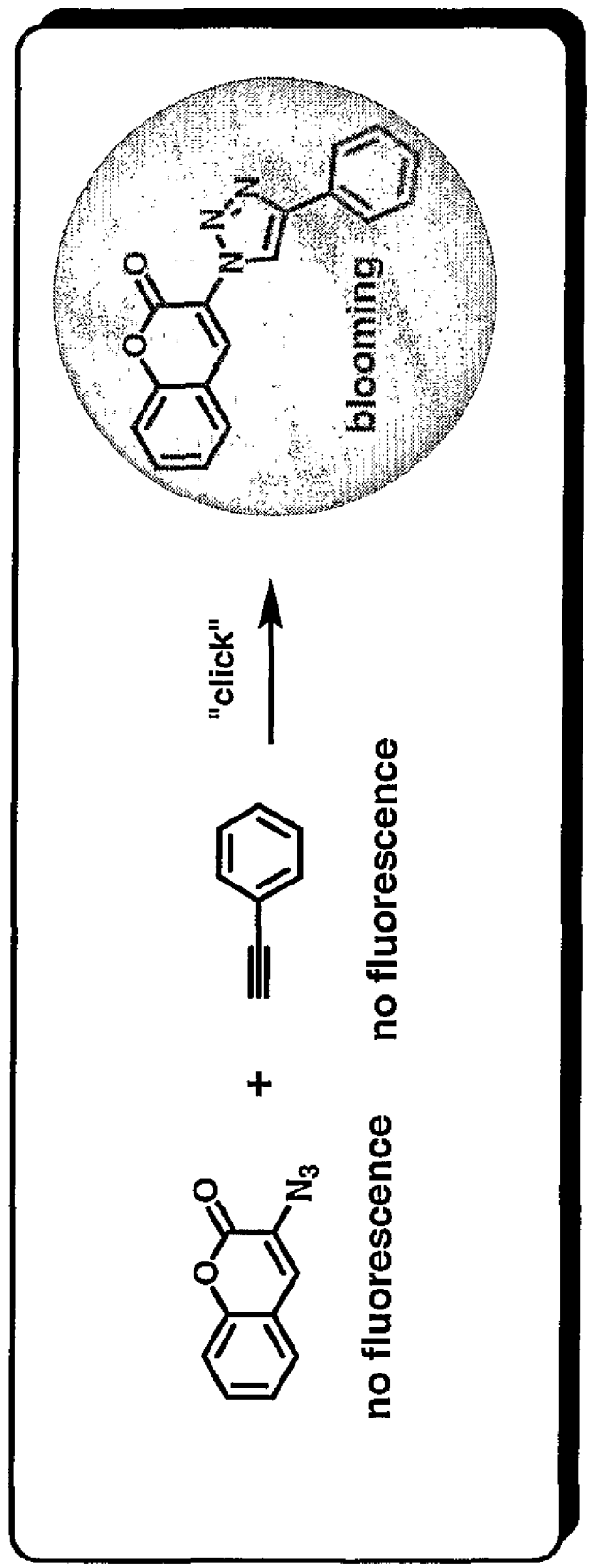
FIG. 1 shows a schematic illustration of an embodiment of the present invention wherein the reaction of azide-substituted coumarin and ethynylbenzene, neither of which has significant fluorescence, forms a fluorescent linkage complex that has a strong fluorescent signal.

In general, the present method involves contacting a first linkage compound having the structure $A\text{-}(Y)_y\text{—}N_3$, or $A\text{-}(Y)_y\text{—}X$, with a second linkage compound having the structure $E\text{-}(Z)_z\text{—}C\equiv CR^E$, or $E\text{-}(Z)_z\text{—}C\equiv N$, to form a linkage complex having a fluorescent signal that is different than the fluorescent signal of the first linkage compound and the fluorescent signal of the second linkage compound. This can be illustrated as shown in FIG. 1, where the reaction of 3-azidocoumarin and phenylacetylene, neither of which are fluorescent, form a linkage complex that has a strong fluorescent signal. In the formulas described above, at least one of A and E is a fluorophore, and any A or E that is not a fluorophore is an organic or inorganic group. Also, X is halo, and when the first linkage compound is $A\text{-}(Y)_y\text{—}X$, the first linkage compound is contacted with the second linkage compound in the presence of an azide salt of lithium, sodium, or potassium. $R^E$ is any chemically possible substituent group. The subscripts y and z are each independently an integer from 0 to 20, and Y and Z are each independently a branched or unbranched alkyl, alkenyl, or alkynyl, which can be substituted or unsubstituted. Accordingly, either Y and/or Z can optionally be present, or can be absent.

When it is said that $R^E$ can be selected from any chemically possible substituent group, it is meant that $R^E$ is selected from —H, $C_1$-$C_6$ alkyl, $C_2$-$C_6$ alkenyl, $C_2$-$C_6$ alkynyl, $C_1$-$C_6$ alkyl-$R^{11}$, $C_2$-$C_6$ alkenyl-$R^{11}$, $C_2$-$C_6$ alkynyl-$R^{11}$, $C_1$-$C_6$ alkyl-$(R^{11})_2$, $C_2$-$C_6$ alkenyl-$(R^{11})_2$, $CSR^{11}$, N=$NR^7$, amino, $CONHR^{11}$, $NHR^7$, $NR^8R^9$, $N(R^7)$—$N(R^8)(R^9)$, $C(R^{11})$=N—$N(R^8)(R^9)$, N=$N(R^7)$, $N(R^7)$—N=$C(R^8)$, $C(R^{11})$=N—$O(R^{10})$, ON=$C(R^{11})$, $C_1$-$C_6$ alkyl-$NHR^7$, $C_1$-$C_6$ alkyl-$NR^8R^9$, $(C_1$-$C_4)$alkyl-$N(R^7)$—$N(R^8)(R^9)$, $(C_1$-$C_4)$alkylC$(R^{11})$=N—$N(R^8)(R^9)$, $(C_1$-$C_4)$alkyl-N=$N(R^7)$, $(C_1$-$C_4)$alkyl-$N(R^7)$—N=$C(R^8)$, nitro, cyano, $CO_2R^{11}$, O—$R^{10}$, $C_1$-$C_4$ alkyl-$OR^{10}$, $COR^{11}$, $SR^{10}$, $SSR^{10}$, $SOR^{11}$, $SO_2R^{11}$, $C_1$-$C_6$ alkyl-$COR^{11}$, $C_1$-$C_6$ alkyl-$SR^{10}$, $C_1$-$C_6$ alkyl-$SOR^{11}$, $C_1$-$C_6$ alkyl-$SO_2R^{11}$, halo, Si$(R^{11})_3$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{12}$;

$R^7$, $R^8$ and $R^9$ are each independently selected from —H, $C_1$-$C_6$ alkyl, $C_2$-$C_6$ alkenyl, $C_2$-$C_6$ alkynyl, $C_1$-$C_4$ alkyl-$R^{11}$, $C_1$-$C_6$ alkyl-$NHR^{13}$, $C_{1-6}$ alkyl-$NR^{13}R^{14}$, O—$R^{15}$, $C_1$-$C_4$ alkyl-$OR^{15}$, $CO_2R^{15}$, $C(S)OR^{15}$, $C(O)SR^{15}$, $C(O)R^{17}$, $C(S)R^{17}$, $CONHR^{16}$, $C(S)NHR^{16}$, $CON(R^{16})_2$, $C(S)N(R^{16})_2$, $SR^{15}$, $SOR^{17}$, $SO_2R^{17}$, $C_1$-$C_6$ alkyl-$CO_2R^{15}$, $C_1$-$C_6$ alkyl-C(S)$OR^{15}$, $C_1$-$C_6$ alkyl-C(O)$SR^{15}$, $C_1$-$C_6$ alkyl-$COR^{17}$, $C_1$-$C_6$ alkyl-C(S)$R^7$, $C_1$-$C_6$ alkyl-$CONHR^{16}$, $C_1$-$C_6$ alkyl-C(S)$NHR^{16}$, $C_1$-$C_6$ alkyl-$CON(R^{16})_2$, $C_1$-$C_6$ alkyl-C(S)$N(R^{16})_2$, $C_1$-$C_6$ alkyl-$SR^{15}$, $C_1$-$C_6$ alkyl-$SOR^{17}$, $C_1$-$C_6$ alkyl-$SO_2R^{17}$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{18}$;

$R^{10}$ is selected from —H, $C_1$-$C_{10}$ alkyl, $C_2$-$C_6$ alkenyl, $C_2$-$C_6$ alkynyl, $C_1$-$C_6$ alkyl-$NHR^{13}$, $C_1$-$C_6$ alkyl-$NR^{13}R^{14}$, $C_1$-$C_4$ alkyl-$OR^{15}$, $CSR^{11}$, $CO_2R^{15}$, $C(S)OR^{15}$, $C(O)SR^{15}$, $COR^7$, $C(S)R^{17}$, $CONHR^{16}$, $C_1$-$C_4$ alkyl-$R^{11}$, $C_1$-$C_4$ alkyl-$NH_2R^{13}$, $C(S)NHR^{16}$, O—$R^{15}$, $CON(R^{16})_2$, $C(S)N(R^{16})_2$, $SOR^7$, $SO_2R^{17}$, $C_1$-$C_6$ alkyl-$CO_2R^{15}$, $C_1$-$C_6$ alkyl-C(S)$OR^{15}$, $C_1$-$C_6$ alkyl-C(O)$SR^{15}$, $C_1$-$C_6$ alkyl-$COR^{17}$, $C_1$-$C_6$ alkyl-C(S)$R^{17}$, $C_1$-$C_6$ alkyl-$CONHR^{16}$, $C_1$-$C_6$ alkyl-C(S)$NHR^{16}$, $C_1$-$C_6$ alkyl-$CON(R^{16})_2$, Si$(R^{13})_2R^{17}$, $C_1$-$C_6$ alkyl-C(S)N$(R^{16})_2$, $C_1$-$C_6$ alkyl-$SR^{15}$, $C_1$-$C_6$ alkyl-$SOR^{17}$, $C_1$-$C_6$ alkyl-$SO_2R^{17}$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{18}$;

$R^{11}$ is selected from —H, $C_1$-$C_6$ alkyl, $C_1$-$C_6$ alkoxy, $C_2$-$C_6$ alkenyl, $C_2$-$C_6$ alkynyl, amino, $NHR^{13}$, $NR^{13}R^{14}$, N=$NR^{13}$, $C_1$-$C_6$ alkyl-$NHR^{13}$, $C_1$-$C_6$ alkyl-$NR^{13}R^{14}$, O—$R^{15}$, $C_1$-$C_4$ alkyl-$OR^{15}$, $SR^{15}$, $COR^{13}CO_2R^{17}$, $C_1$-$C_6$ alkyl-$CO_2R^{15}$, $C_1$-$C_6$ alkyl-C(S)$OR^{15}$, $C_1$-$C_6$ alkyl-C(O)$SR^{15}$, $C_1$-$C_6$ alkyl-$COR^{17}$, $C_1$-$C_6$ alkyl-C(S)$R^{17}$, $C_1$-$C_6$ alkyl-$CONHR^{16}$, $C_1$-$C_6$ alkyl-C(S)$NHR^{16}$, $C_1$-$C_6$ alkyl-$CON(R^{16})_2$, $C_1$-$C_6$ alkyl-C(S)$N(R^{16})_2$, $C_1$-$C_6$ alkyl-$SR^{15}$, $C_1$-$C_6$ alkyl-$SOR^{17}$, $C_1$-$C_6$ alkyl-$SO_2R^{17}$, halo, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{18}$;

$R^{12}$ is selected from —H, OH, oxo, $C_1$-$C_{10}$ alkyl, $C_2$-$C_{10}$ alkenyl, $C_2$-$C_{10}$ alkynyl, $C_1$-$C_{10}$ alkyl-$R^{11}$, $C_2$-$C_{10}$ alkenyl-$R^{11}$, $C_2$-$C_{10}$ alkynyl-$R^{11}$, $C_1$-$C_{10}$ alkyl-$(R^{11})_2$, $C_2$-$C_{10}$ alkenyl-$(R^{11})_2$, $CSR^{11}$, N=$NR^7$, hydroxyl $C_1$-$C_6$ alkyl-$R^{11}$, amino $C_1$-$C_4$ alkyl-$R^7$, amino, $NHR^7$, $NR^8R^9$, $N(R^7)$—$N(R^8)(R^9)$, $C(R^{11})$=N—$N(R^8)(R^9)$, N=$N(R^7)$, $N(R^7)$—N=$C(R^8)$, $C(R^{11})$=N—$O(R^{10})$, ON=$C(R^{11})$, $C_1$-$C_{10}$ alkyl-$NHR^7$, $C_1$-$C_{10}$ alkyl-$NR^8R^9$, $(C_1$-$C_{10})$alkyl-$N(R^7)$—$N(R^8)(R^9)$, $(C_1$-$C_{10})$alkylC$(R^{11})$=N—$N(R^8)(R^9)$, $(C_1$-$C_{10})$alkyl-N=$N(R^7)$, $(C_1$-$C_{10})$alkyl-$N(R^7)$—N=$C(R^8)$, SCN, NCS, $C_1$-$C_{10}$ alkyl SCN, $C_1$-$C_{10}$ alkyl NCS, nitro, cyano, O—$R^{10}$, $C_1$-$C_{10}$ alkyl-$OR^{10}$, $COR^{11}$, $CO_2R^{11}$, $SR^{10}$, $SSR^{10}$, $SOR^{11}$, $SO_2R^{11}$, $C_1$-$C_{10}$ alkyl-$COR^{11}$, $C_1$-$C_{10}$ alkyl-$SR^{10}$, $C_1$-$C_{10}$ alkyl-$SOR^{11}$, $C_1$-$C_{10}$ alkyl-$SO_2R^{11}$, halo, Si$(R^{11})_3$, halo $C_1$-$C_{10}$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{18}$;

$R^{13}$ and $R^{14}$ are each independently selected from —H, oxo, $C_1$-$C_6$ alkyl, $C_2$-$C_6$ alkenyl, $C_2$-$C_6$ alkynyl, $C_1$-$C_4$ alkyl-$R^{23}$, $C_1$-$C_6$ alkyl-$NHR^{19}$, $C_1$-$C_6$ alkyl-$NR^{19}R^{20}$, O—$R^{21}$, $C_1$-$C_4$ alkyl-$OR^{21}$, $CO_2R^{21}$, $COR^{21}$, $C(S)OR^{21}$, $C(O)SR^{21}$, $C(O)R^{23}$, $C(S)R^{23}$, $CONHR^{22}$, $C(S)NHR^{22}$, $CON(R^{22})_2$, $C(S)N(R^{22})_2$, $SR^{21}$, $SOR^{23}$, $SO_2R^{23}$, $C_1$-$C_6$ alkyl-C(S)$OR^{21}$, $C_1$-$C_6$ alkyl-C(O)$SR^{21}$, $C_1$-$C_6$ alkyl-$COR^{23}$, $C_1$-$C_6$ alkyl-C(S)$R^{23}$, C1-$C_6$ alkyl-$CONHR^{22}$, C1-$C_6$ alkyl-C(S)$NHR^{22}$, $C_1$-$C_6$ alkyl-$CON(R^{22})_2$, $C_1$-$C_6$ alkyl-C(S)$N(R^{22})_2$, $C_1$-$C_6$ alkyl-$SR^{21}$, $C_1$-$C_6$ alkyl-$SOR^{23}$, $C_1$-$C_6$ alkyl-$SO_2R^{23}$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{24}$;

$R^{15}$ and $R^{16}$ are independently selected from —H, $C_1$-$C_6$ alkyl, $C_2$-$C_6$ alkenyl, $C_2$-$C_6$ alkynyl, $C_1$-$C_6$ alkyl-$NHR^{19}$, $C_1$-$C_6$ alkyl-$NR^{19}R^{20}$, $C_1$-$C_4$ alkyl-$OR^{21}$, $CSR^{11}$, $CO_2R^{22}$, $COR^{23}$, $CONHR^{22}$, $CON(R^{22})_2$, $SOR^{23}$, $SO_2R^{23}$, $C_1$-$C_6$ alkyl-$CO_2R^{22}$, $C_1$-$C_6$ alkyl-$COR^{23}$, $C_1$-$C_6$ alkyl-$CONHR^{22}$, $C_1$-$C_6$ alkyl-$CON(R^{22})_2$, $C_1$-$C_6$ alkyl-$SR^{21}$, $C_1$-$C_6$ alkyl-$SOR^{23}$, $C_1$-$C_6$ alkyl-$SO_2R^{23}$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{24}$;

$R^{17}$ is selected from —H, $C_1$-$C_6$ alkyl, $C_2$-$C_6$ alkenyl, $C_2$-$C_6$ alkenyl-$R^{19}$, $C_1$-$C_6$ alkyl-$R^{19}$, $C_2$-$C_6$ alkynyl, amino, $NHR^{19}$, $NR^{19}R^{20}$, $C_1$-$C_6$ alkyl-$NHR^{19}$, $C_1$-$C_6$ alkyl-$NR^{19}R^{20}$, O—$R^{21}$, $C_1$-$C_4$ alkyl-$OR^{21}$, $SR^{21}$, $C_1$-$C_6$ alkyl- $CO_2R^{21}$, $C_1$-$C_6$ alkyl-C(S)O$R^{21}$, $C_1$-$C_6$ alkyl-C(O)S$R^{21}$, $C_1$-$C_6$ alkyl-CO$R^{23}$, $C_1$-$C_6$ alkyl-C(S)$R^{23}$, $C_1$-$C_6$ alkyl-CONH$R^{22}$, $C_1$-$C_6$ alkyl-C(S)NH$R^{22}$, $C_1$-$C_6$ alkyl-CON($R^{22}$)$_2$, $C_1$-$C_6$ alkyl-C(S)N($R^{22}$)$_2$, $C_1$-$C_6$ alkyl-S$R^{21}$, $C_1$-$C_6$ alkyl-SO$R^{23}$, $C_1$-$C_6$ alkyl-SO$_2R^{23}$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{24}$;

$R^{18}$ is selected from —H, oxo, OH, $C_1$-$C_{10}$ alkyl, $C_2$-$C_{10}$ alkenyl, $C_2$-$C_{10}$ alkynyl, $C_1$-$C_{10}$ alkyl-$R^{23}$, $C_2$-$C_{10}$ alkenyl-$R^{23}$, $C_2$-$C_{10}$ alkynyl-$R^{23}$, $C_1$-$C_{10}$ alkyl-($R^{23}$)$_2$, $C_2$-$C_{10}$ alkenyl-($R^{23}$)$_2$, CS$R^{23}$, N=N$R^{19}$, amino, NH$R^{19}$, N$R^{20}R^{20}$, N($R^{19}$)—N($R^{20}$)($R^{20}$), C($R^{23}$)=N—N($R^{20}$)($R^{20}$), N=N($R^{19}$), N($R^{19}$)—N=C($R^{20}$), C($R^{23}$)=N—O($R^{21}$), ON=C($R^{23}$), $C_1$-$C_{10}$ alkyl-NH$R^{19}$, $C_1$-$C_{10}$ alkyl-N$R^{20}R^{20}$, ($C_1$-$C_{10}$)alkyl-N($R^{19}$)—N($R^{20}$)($R^{20}$), ($C_1$-$C_{10}$)alkylC($R^{23}$)=N—N($R^{20}$)($R^{20}$), ($C_1$-$C_{10}$)alkyl-N=N($R^{19}$), ($C_1$-$C_{10}$)alkyl-N($R^{19}$)—N=C($R^{20}$), SCN, NCS, $C_1$-$C_{10}$ alkyl SCN, $C_1$-$C_{10}$ alkyl NCS, nitro, cyano, O—$R^{21}$, $C_1$-$C_{10}$ alkyl-O$R^{21}$, CO$R^{23}$, CO$_2R^{23}$, S$R^{21}$, SS$R^{21}$% SO$R^{23}$, SO$_2R^{23}$, $C_1$-$C_{10}$ alkyl-CO$R^{23}$, $C_1$-$C_{10}$ alkyl-S$R^{21}$, $C_1$-$C_{10}$ alkyl-SO$R^{23}$, $C_1$-$C_{10}$ alkyl-SO$_2R^{23}$, halo, Si($R^{23}$)$_3$, halo $C_1$-$C_{10}$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{24}$;

$R^{19}$ and $R^{20}$ are each independently selected from —H, $C_1$-$C_6$ alkyl, $C_2$-$C_6$ alkenyl, $C_2$-$C_6$ alkynyl, $C_1$-$C_4$ alkyl-$R^{29}$, $C_1$-$C_6$ alkyl-NH$R^{25}$, $C_1$-$C_6$ alkyl-N$R^{25}R^{26}$, O—$R^{27}$, $C_1$-$C_4$ alkyl-O$R^{27}$, CO$_2R^{27}$, C(S)O$R^{27}$, C(O)S$R^{27}$, C(O)$R^{29}$, C(S)$R^{29}$, CONH$R^{28}$, C(S)NH$R^{28}$, CON($R^{28}$)$_2$, C(S)N($R^{28}$)$_2$, S$R^{27}$, SO$R^{29}$, SO$_2R^{29}$, $C_1$-$C_6$ alkyl-CO$_2R^{27}$, $C_1$-$C_6$ alkyl-C(S)O$R^{27}$, $C_1$-$C_6$ alkyl-C(O)S$R^{27}$, $C_1$-$C_6$ alkyl-CO$R^{29}$, $C_1$-$C_6$ alkyl-C(S)$R^{29}$, $C_1$-$C_6$ alkyl-CONH$R^{28}$, $C_1$-$C_6$ alkyl-C(S)NH$R^{28}$, $C_1$-$C_6$ alkyl-CON($R^{28}$)$_2$, $C_1$-$C_6$ alkyl-C(S)N($R^{28}$)$_2$, $C_1$-$C_6$ alkyl-S$R^{27}$, $C_1$-$C_6$ alkyl-SO$R^{29}$, $C_1$-$C_6$ alkyl-SO$_2R^{29}$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{30}$;

$R^{21}$ and $R^{22}$ are independently selected from —H, $C_1$-$C_{10}$ alkyl, $C_2$-$C_6$ alkenyl, $C_2$-$C_6$ alkynyl, $C_1$-$C_6$ alkyl-NH$R^{25}$, $C_1$-$C_6$ alkyl-N$R^{25}R^{26}$, $C_1$-$C_4$ alkyl-O$R^{27}$, CS$R^{11}$, CO$_2R^{28}$, CO$R^{29}$, CONH$R^{28}$, CON($R^{28}$)$_2$, SO$R^{29}$, SO$_2R^{29}$, $C_1$-$C_6$ alkyl-CO$_2R^{28}$, $C_1$-$C_6$ alkyl-CO$R^{29}$, $C_1$-$C_6$ alkyl-CONH$R^{28}$, $C_1$-$C_6$ alkyl-CON($R^{28}$)$_2$, $C_1$-$C_6$ alkyl-S$R^{27}$, $C_1$-$C_6$ alkyl-SO$R^{29}$, $C_1$-$C_6$ alkyl-SO$_2R^{29}$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{30}$;

$R^{23}$ is selected from —H, $C_1$-$C_6$ alkyl, $C_2$-$C_6$ alkenyl, $C_2$-$C_6$ alkenyl-$R^{25}$, $C_1$-$C_6$ alkyl-$R^{25}$, $C_2$-$C_6$ alkynyl, amino, NH$R^{25}$, N$R^{25}R^{26}$, $C_1$-$C_6$ alkyl-NH$R^{25}$, $C_1$-$C_6$ alkyl-N$R^{25}R^{26}$, O—$R^{27}$, $C_1$-$C_4$ alkyl-O$R^{27}$, S$R^{27}$, $C_1$-$C_6$ alkyl-CO$_2R^{27}$, $C_1$-$C_6$ alkyl-C(S)O$R^{27}$, $C_1$-$C_6$ alkyl-C(O)S$R^{27}$, $C_1$-$C_6$ alkyl-CO$R^{29}$, $C_1$-$C_6$ alkyl-C(S)$R^{29}$, $C_1$-$C_6$ alkyl-CONH$R^{28}$, $C_1$-$C_6$ alkyl-C(S)NH$R^{28}$, $C_1$-$C_6$ alkyl-CON($R^{28}$)$_2$, $C_1$-$C_6$ alkyl-C(S)N($R^{28}$)$_2$, $C_1$-$C_6$ alkyl-S$R^{27}$, $C_1$-$C_6$ alkyl-SO$R^{29}$, $C_1$-$C_6$ alkyl-SO$_2R^{29}$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{30}$;

$R^{24}$ is selected from —H, OH, $C_1$-$C_{10}$ alkyl, $C_2$-$C_{10}$ alkenyl, $C_2$-$C_{10}$ alkynyl, $C_1$-$C_{10}$ alkyl-$R^{29}$, $C_2$-$C_{10}$ alkenyl-$R^{29}$, $C_2$-$C_{10}$ alkynyl-$R^{29}$, $C_1$-$C_{10}$ alkyl-($R^{29}$)$_2$, $C_2$-$C_{10}$ alkenyl-($R^{29}$)$_2$, CS$R^{29}$, N=N$R^{25}$, amino, NH$R^{25}$, N$R^{26}R^{26}$, N($R^{25}$)—N($R^{26}$)($R^{26}$), C($R^{29}$)=N—N($R^{26}$)($R^{26}$), N=N($R^{25}$), N($R^{25}$)—N=C($R^{26}$), C($R^{29}$)=N—O($R^{27}$), ON=C($R^{29}$), $C_1$-$C_{10}$ alkyl-NH$R^{25}$, $C_1$-$C_{10}$ alkyl-N$R^{26}R^{26}$, ($C_1$-$C_{10}$) alkyl-N($R^{25}$)—N($R^{26}$)($R^{26}$), ($C_1$-$C_{10}$)alkylC($R^{29}$)=N—N($R^{26}$)($R^{26}$), ($C_1$-$C_{10}$)alkyl-N=N($R^{25}$), ($C_1$-$C_{10}$)alkyl-N($R^{25}$)—N=C($R^{26}$), SCN, NCS, $C_1$-$C_{10}$ alkyl SCN, $C_1$-$C_{10}$ alkyl NCS, nitro, cyano, O—$R^{27}$, $C_1$-$C_{10}$ alkyl-O$R^{27}$, CO$_2R^{29}$, CO$R^{29}$, S$R^{27}$, SS$R^{27}$, SO$R^{29}$, SO$_2R^{29}$, $C_1$-$C_{10}$ alkyl-CO$R^{29}$, $C_1$-$C_{10}$ alkyl-S$R^{27}$, $C_1$-$C_{10}$ alkyl-SO$R^{29}$, $C_1$-$C_{10}$ alkyl-SO$_2R^{29}$, halo, Si($R^{29}$)$_3$, halo $C_1$-$C_{10}$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{30}$;

$R^{25}$ and $R^{26}$ are each independently selected from —H, $C_1$-$C_6$ alkyl, $C_2$-$C_6$ alkenyl, $C_2$-$C_6$ alkynyl, $C_1$-$C_4$ alkyl-$R^{35}$, $C_1$-$C_6$ alkyl-NH$R^{31}$, $C_1$-$C_6$ alkyl-N$R^{31}R^{32}$, O—$R^{33}$, $C_1$-$C_4$ alkyl-O$R^{33}$, CO$_2R^{33}$, C(S)O$R^{33}$, C(O)S$R^{33}$, C(O)$R^{35}$, C(S)$R^{35}$, CONH$R^{34}$, C(S)NH$R^{34}$, CON($R^{34}$)$_2$, C(S)N($R^{34}$)$_2$, S$R^{33}$, SO$R^{35}$, SO$_2R^{35}$, $C_1$-$C_6$ alkyl-CO$_2R^{33}$, $C_1$-$C_6$ alkyl-C(S)O$R^{33}$, $C_1$-$C_6$ alkyl-C(O)S$R^{33}$, $C_1$-$C_6$ alkyl-CO$R^{35}$, $C_1$-$C_6$ alkyl-C(S)$R^{35}$, $C_1$-$C_6$ alkyl-CONH$R^{34}$, $C_1$-$C_6$ alkyl-C(S)NH$R^{34}$, $C_1$-$C_6$ alkyl-CON($R^{34}$)$_2$, $C_1$-$C_6$ alkyl-C(S)N($R^{34}$)$_2$, $C_1$-$C_6$ alkyl-S$R^{33}$, $C_1$-$C_6$ alkyl-SO$R^{35}$, $C_1$-$C_6$ alkyl-SO$_2R^{35}$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{36}$;

$R^{27}$ and $R^{28}$ are independently selected from —H, $C_1$-$C_6$ alkyl, $C_2$-$C_6$ alkenyl, $C_2$-$C_6$ alkynyl, $C_1$-$C_6$ alkyl-NH$R^{31}$, $C_1$-$C_6$ alkyl-N$R^{31}R^{32}$, $C_1$-$C_4$ alkyl-O$R^{33}$, CS$R^{35}$, CO$_2R^{34}$, CO$R^{35}$, CONH$R^{34}$, CON($R^{34}$)$_2$, SO$R^{35}$, SO$_2R^{35}$, $C_1$-$C_6$ alkyl-CO$_2R^{34}$, $C_1$-$C_6$ alkyl-CO$R^{35}$, $C_1$-$C_6$ alkyl-CONH$R^{34}$, $C_1$-$C_6$ alkyl-CON($R^{34}$)$_2$, $C_1$-$C_6$ alkyl-S$R^{33}$, $C_1$-$C_6$ alkyl-SO$R^{35}$, $C_1$-$C_6$ alkyl-SO$_2R^{35}$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{36}$;

$R^{29}$ is selected from —H, $C_1$-$C_6$ alkyl, $C_2$-$C_6$ alkenyl, $C_2$-$C_6$ alkenyl-$R^{31}$, $C_1$-$C_6$ alkyl-$R^{31}$, $C_2$-$C_6$ alkynyl, amino, NHR$^{31}$, NR$^{31}$R$^{32}$, $C_1$-$C_6$ alkyl-NHR$^{31}$, $C_1$-$C_6$ alkyl-NR$^{31}$R$^{32}$, O—R$^{33}$, $C_1$-$C_4$ alkyl-OR$^{33}$, SR$^{33}$, $C_1$-$C_6$ alkyl-CO$_2$R$^{33}$, $C_1$-$C_6$ alkyl-C(S)OR$^{33}$, $C_1$-$C_6$ alkyl-C(O)SR$^{33}$, $C_1$-$C_6$ alkyl-COR$^{35}$, $C_1$-$C_6$ alkyl-C(S)R$^{35}$, $C_1$-$C_6$ alkyl-CONHR$^{34}$, $C_1$-$C_6$ alkyl-C(S)NHR$^{34}$, $C_1$-$C_6$ alkyl-CON(R$^{34}$)$_2$, $C_1$-$C_6$ alkyl-C(S)N(R$^{34}$)$_2$, $C_1$-$C_6$ alkyl-SR$^{33}$, $C_1$-$C_6$ alkyl-SOR$^{35}$, $C_1$-$C_6$ alkyl-SO$_2$R$^{35}$, halo $C_1$-$C_4$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{36}$;

$R^{30}$ is selected from —H, OH, $C_1$-$C_{10}$ alkyl, $C_2$-$C_{10}$ alkenyl, $C_2$-$C_{10}$ alkynyl, $C_1$-$C_{10}$ alkyl-$R^{35}$, $C_2$-$C_{10}$ alkenyl-$R^{35}$, $C_2$-$C_{10}$ alkynyl-$R^{35}$, $C_1$-$C_{10}$ alkyl-($R^{35}$)$_2$, $C_2$-$C_{10}$ alkenyl-($R^{35}$)$_2$, CSR$^{35}$, N=NR$^{31}$, amino, NHR$^{31}$, NR$^{32}$R$^{32}$, N(R$^{31}$)—N(R$^{32}$)(R$^{32}$), C(R$^{35}$)=N—N(R$^{32}$)(R$^{32}$), N=N(R$^{31}$), N(R$^{31}$)—N=C(R$^{32}$), C(R$^{35}$)=N—O(R$^{33}$), ON=C(R$^{35}$), $C_1$-$C_{10}$ alkyl-NHR$^{31}$, $C_1$-$C_{10}$ alkyl-NR$^{32}$R$^{32}$, ($C_1$-$C_{10}$)alkyl-N(R$^{31}$)—N(R$^{32}$)(R$^{32}$), ($C_1$-$C_{10}$)alkylC(R$^{35}$)=N—N(R$^{32}$)(R$^{32}$), ($C_1$-$C_{10}$)alkyl-N=N(R$^{31}$), ($C_1$-$C_{10}$)alkyl-N(R$^{31}$)—N=C(R$^{32}$), SCN, NCS, $C_1$-$C_{10}$ alkyl SCN, $C_1$-$C_{10}$ alkyl NCS, nitro, cyano, O—R$^{33}$, $C_1$-$C_{10}$ alkyl-OR$^{33}$, COR$^{35}$, SR$^{33}$, SSR$^{33}$, SOR$^{35}$, SO$_2$R$^{35}$, $C_1$-$C_{10}$ alkyl-COR$^{35}$, $C_1$-$C_{10}$ alkyl-SR$^{33}$, $C_1$-$C_{10}$ alkyl-SOR$^{35}$, $C_1$-$C_{10}$ alkyl-SO$_2$R$^{35}$, halo, Si(R$^{35}$)$_3$, halo $C_1$-$C_{10}$ alkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{36}$;

$R^{31}$, $R^{32}$, $R^{33}$ and $R^{34}$ are each independently selected from —H, alkyl, alkenyl, alkynyl, aminoalkyl, hydroxyalkyl, alkylamino alkyl, dialkylaminoalkyl, alkoxyalkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{36}$;

$R^{35}$ is selected from —H, alkyl, alkenyl, alkynyl, aminoalkyl, OH, alkoxy, amino, alkylamino, dialkylamino, hydroxyalkyl, alkylamino alkyl, dialkylaminoalkyl, alkoxyalkyl, aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl, wherein aryl, heteroaryl, heterocyclyl, alkylaryl, alkylheterocyclyl, alkylheteroaryl, arylalkyl, heteroarylalkyl, heterocyclylalkyl, and $C_1$-$C_{10}$ mono- and bicyclic cycloalkyl are optionally substituted with one or more of the groups defined by $R^{36}$; and $R^{36}$ is selected from —H, alkyl, alkenyl, alkynyl, aminoalkyl, OH, alkoxy, amino, nitro, cyano, halo, alkylamino, dialkylamino, hydroxyalkyl, alkylamino alkyl, dialkylaminoalkyl, alkoxyalkyl, aryl, heteroaryl, heterocyclyl, cycloalkyl, alkylaryl, alkylheterocyclyl, alkylheteroaryl, arylalkyl, heterocyclylalkyl, and heteroarylalkyl. In some embodiments, it is preferred that $R^E$ is hydrogen.

As the term "fluorophore" is used herein, it should be understood to mean an organic compound that has little or no fluorescent signal when it is substituted with at least one azido (—N$_3$), cyano (—C≡N, or —CN), or alkyne group (—C≡CR$^E$, or —≡), but which has a fluorescent signal when the azido, cyano, or alkyne substituent group of the fluorophore reacts with a cyano group or an alkyne, or with an azido group, respectively, of a separate substance to form a triazole or tetrazole linkage complex. Without being bound by this or any other theory, it is believed that the fluorescent signal of the fluorophore is quenched by the pendent azido, cyano, or alkyne, but the reaction of that group with a suitable reactant group to form a linkage complex removes the quenching effect of the substituent group and the linkage complex is fluorescent. The term "fluorophore" also includes organic compounds that have a fluorescent signal when substituted with at least one azido, cyano group, or alkyne group, but when the substituent group of the fluorophore reacts with a cyano group or an alkyne, or with an azido group, respectively, of a separate substance to form a triazole or tetrazole linked to the fluorophore to form a linkage complex, the linkage complex has a fluorescent signal at a wavelength that is different than the fluorophore.

Figure 2:
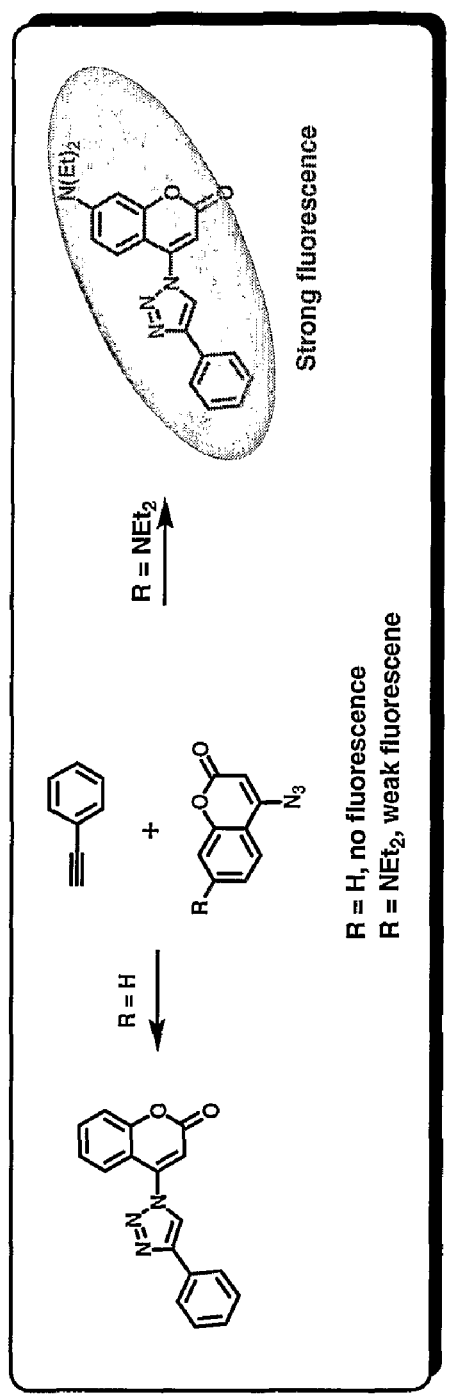
FIG. 2 is a schematic illustration of an embodiment of the present method in which the chemoselective reaction of a fluorophore having an azide substituent, which has a weak fluorescent signal, with a group having an alkyne produces a linkage complex that provides a strong fluorescent signal, and also shows that the addition of different functional groups on the fluorophore permits controlled change in the type of fluorescent signal that is characteristic of the linkage complex.

By way of example as shown in FIG. 2, an azido-substituted fluorophore, such as 4-azidocoumarin, has little or no fluorescent signal, but when the azido group is reacted with an alkyne, such as provided by phenyl acetylene, to form a triazole linkage complex, the reaction product is fluorescent.

Examples of materials that can act as the fluorophore of the present method include fluorescein, eosin, erythrosin, Oregon-green, naphthofluorescein, rhodol, rhodamine, Texas Red, polymethine dyes, cyanine, hemicyanine, streptocyanine, sulfo and aza derivatives of rhodamine, resorufin, boron dipyrromethene derivatives (BODIPY), connexin, azo dyes, malachite green, isosulfan blue, naphthalene derivatives, dansyl dyes, anthracene derivatives, pyrene derivatives pyridyloxazoles, or coumarin. In preferred embodiments, the fluorophore is a substituted or unsubstituted coumarin, rhodamine, or fluorescein. It is more preferred that the fluorophore is a substituted or unsubstituted coumarin.

As discussed above, the present method comprises the reaction of two reactants, a first linkage compound and a second linkage compound, to form a linkage complex. In one embodiment of this method, neither the first linkage compound nor the second linkage compound is fluorescent, but fluorescence is "turned on" by the conjugation reaction and formation of the linkage complex. In another embodiment, one or both of the first and second linkage compounds have a fluorescent signal, but the conjugated product—the linkage complex—has stronger fluorescence, or a fluorescent signal at a wavelength that is different than exhibited by either the first or the second linkage compound.

An embodiment of the present invention comprises a bioconjugation method based on a 1,3-dipolar cycloaddition reaction between an azide and an alkyne. Under mild conditions, catalyzed with copper(I), an azide and an alkyne can form a triazole ring as shown in equation 1. Azide, alkyne and triazole species are known to be biocompatible. See, e.g., Wang, Q. et al., *J. Am. Chem. Soc.* 125: 3192-3193 (2003), Speers, A. E. et al., *J Am Chem Soc.* 125: 4686-7 (2003), Seo, T. S. et al., *J Org Chem.* 68: 609-12 (2003), Lewis, W. G. et al., *Angew Chem Int Ed Engl.* 41: 1053-7 (2002), and Lee, L. V. et al. *J Am Chem Soc.* 125: 9588-9 (2003). Therefore, azide and alkyne derivatives can be used as biocompatible linkers.

In an embodiment of the present invention two types of linkage compounds are used. Examples of these two types of linkers are shown in equation 1, below, where one type of linkage compound is an alkyne and another type is an azide.

Equation 1:

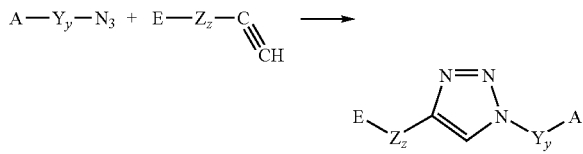

Both of the linkage compounds are non-fluorescent and have high fidelity for bioconjugation to each other under mild conditions. However, the conjugation reaction forms a highly fluorescent probe, which can be used to detect the conjugated product. When the reactive groups on the linkage compounds comprise an azido group and an alkyne, the conjugation can be catalyzed with copper(I) at physiological conditions of temperature, pressure, and pH to yield a triazole linkage complex. In one example, when the linkage compounds are 3-azidocoumarin and phenyl acetylene, the linkage complex that is formed (3-(4-phenyl-[1,2,3]triazol-1-yl)-chromen-2-one) has a fluorescent signal at a wavelength around 478 nm due to the elimination of the quenching by formation of the triazole ring.

In an example of a useful first linkage compound of the present invention, the "A" group includes a substituted coumarin compound, and the first linkage compound comprises a compound having the structure shown in Structure 1:

Structure 1:

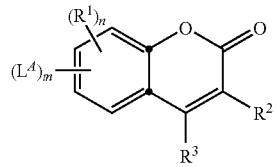

where:
  n is an integer from 0 to 4;
  m is 0 or 1;
  each $R^1$ is the same or different and is any chemically possible substituent group, optionally two or more $R^1$ groups join to form one or more substituted or unsubstituted rings;
  at least one of $R^2$ and $R^3$ is —$(Y)_y$—$N_3$, or —$(Y)_y$—X, and the other is any $R^1$ group;
  Y is a branched or unbranched alkyl, alkenyl, or alkynyl, which can be substituted or unsubstituted;
  y is an integer from 0 to 20;
  X is chloro, bromo, or iodo; and
  $L^A$ is a linking group.

In another embodiment, the first linkage compound has the structure described in structure 1, except that:
  at least one of $R^2$ and $R^3$ is —$(Y)_y$—$N_3$, or —$(Y)_y$—X, and the other is any $R^1$ group; and
  n is an integer from 0 to 4;
  m is 0 or 1; and
  each $R^1$ is the same or different and is selected from hydrogen, hydroxyl, alkyl, alkenyl, alkynyl, halo, carboxyl, carbonyl, alkyloxyl, alkoxyl, alkoxyalkyl, amino, alkylamino, azido, hydroxyalkyl, sulfonyl, sulfinyl, phospho, phosphino, or optionally two or more $R^1$ groups join to form one or more substituted or unsubstituted rings.

In a more preferred embodiment, the first linking compound has the structure described in structure 1, except that at least one of $R^2$ and $R^3$ is —$(Y)_y$—$N_3$.

Examples of the first linkage compound having an azido group are shown below in Table 1.

TABLE 1

| Examples of first linkage compound having azido groups. |
| --- |
| A. 3-azidocoumarin, |
| B. 3-azido-7-hydroxycoumarin, |
| C. 3-azido-7-methoxycoumarin, |
| D. 3-azido-7-acetylcoumarin, |
| E. 3-azido-7-diethylaminocoumarin, |
| F. 9-azido-2,3,5,6-tetrahydro-1H,4H-11-oxa-3a-aza-benzo[de]anthracen-10-one, |
| G. 3-azido-6-bromocoumarin, |
| H. 3-azido-8-ethoxycoumarin. |
| I. 4-azidocoumarin, |
| J. 3-azido-7-acetamidocoumarin, |
| K. 4-azido-7-diethylaminocoumarin, |

In the preferred first linkage compound that is described in structure 1, the group $L^A$ is termed a linking group. The linking group is chemically linked to the first linkage compound and has at least one reactive group that is free for chemical reaction with another material, such as a biomolecule. Typically, $L^A$ is an organic substituent group which has at least one reactive group that is selected from carboxylic acid esters, sulfonyl halide, acyl halide, aldehydes, reactive ketones, aromatic halides, bromoacetamides, idoacetamides, maleimides, disulfides, hydroxyl, amines, diazonium compounds, active alkylating reagents, active acylating reagents, or diketones. It is preferred that the $L^A$ group is an organic substituent group that is selected from branched or unbranched $C_1$-$C_{12}$ alkyl, $C_1$-$C_{12}$ alkenyl, $C_1$-$C_{12}$ alkynyl, or aryl, heteroaryl, or heterocyclyl, and which has at least one substituent reactive group that is selected from carboxylic acid esters, sulfonyl halide, acyl halide, aldehydes, reactive ketones, aromatic halides, bromoacetamides, idoacetamides, maleimides, disulfides, hydroxyl, amines, diazonium compounds, active alkylating reagents, active acylating reagents, or diketones.

In an alternative embodiment, the first linkage compound has the structure shown in structure 1, except that at least one of $R^2$ and $R^3$ is —$(Y)_y$—X. Typically, X is selected from Br, or Cl. In this embodiment, it is preferred that coumarin is substituted at carbon 7 with a group selected from hydrogen, hydroxyl, amino, alkyl, alkenyl, alkoxyl, or alkylamine; and the $R^2$ or $R^3$ that is not —$(Y)_y$—X is selected from hydrogen, amino, nitro, carboxyl, hydroxyl, $C_1$-$C_4$ alkyl, or halo. When at least one of $R^2$ and $R^3$ is —$(Y)_y$—X, the first linkage compound is contacted with the second linkage compound in the presence of an azide salt of an alkali metal, or alkali earth metal. In particular, azide salts of lithium, sodium, or potassium are preferred. In addition, when the first linkage compound comprises a halide, it is common to contact the first and the second linkage compounds in the presence of a Cu(I) catalyst.

In a preferred embodiment, the first linkage compound is a 3-halocoumarin or a 4-halocoumarin, where the coumarin is either unsubstituted, or is substituted at position 7 with hydroxyl, amino, nitro, alkylamino, dialkylamino, or $C_1$-$C_6$ alkyl, and optionally is substituted at whichever of position 3 or 4 not having a halo substituent with amino, nitro, carboxyl, hydroxyl, or $C_1$-$C_6$ alkyl. Alternatively, both the 3 and 4 positions of coumarin can be substituted with halo.

In a preferred embodiment of the present method, the first linkage compound is chemically bonded to a biomaterial. Examples of biomaterials that are useful in the present method include small molecules (such as, for examples, drugs, ligands and catalysts), or peptides, proteins, nucleic acids, oligonucleotides, saccharides, viruses, cells, organic polymers, inorganic polymers, nanoparticles, or solid surfaces, and the like.

It is also preferred that when the "A" group of the first linkage compound comprises a fluorophore, the "E" group of the second linkage compound does not comprise a fluorophore. Therefore, when the "A" group of the first linkage compound comprises a substituted or unsubstituted coumarin, such as shown in structure 1, the "E" group of the second linkage compound can comprise hydrogen, hydroxyl, carboxyl, amino, alkylamino, or a substituted or unsubstituted alkyl, alkenyl, alkynyl, alkoxy, alkoxyalkyl, alkoxyalkenyl, carboxyalkyl, amino, aminoalkyl, aryl, heteroaryl, or heterocyclyl, and if substituted, at least one substituent is optionally $L^B$, where $L^B$ is a linking group that can be the same as, or is similar to $L^A$, and which will be discussed below.

In an example of a useful second linkage compound of the present invention, the "E" group includes a substituted coumarin compound, and the second linkage compound comprises a compound having the structure shown in Structure 2, below:

Structure 2:

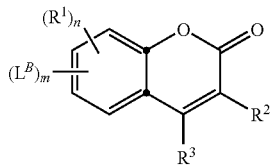

where:

n is an integer from 0 to 4;

m is 0 or 1;

each $R^1$ is the same or different and is any chemically possible substituent group, optionally two or more $R^1$ groups join to form one or more substituted or unsubstituted rings;

at least one of $R^2$ and $R^3$ is $—(Z)_z—C≡CR^E$, or $—(Z)_z—C≡N$, and the other is any $R^1$ group;

Z is a branched or unbranched alkyl, alkenyl, or alkynyl, which can be substituted or unsubstituted;

$R^E$ is selected from any chemically possible substituent group;

z is an integer from 0 to 20; and $L^B$ is a linking group.

As an alternative, the second linkage compound has a structure as shown in structure 2, except that at least one of $R^2$ and $R^3$ is $—(Z)_z—C_1≡CR^E$, or $—(Z)_z—C≡N$, and the other is any $R^1$ group; and n is an integer from 0 to 4;

m is 0 or 1; and each $R^1$ is the same or different and is selected from hydrogen, hydroxyl, alkyl, alkenyl, alkynyl, halo, carboxyl, carbonyl, alkyloxyl, alkoxyl, alkoxyalkyl, amino, alkylamino, azido, hydroxyalkyl, sulfonyl, sulfinyl, phospho, phosphino, or optionally two or more $R^1$ groups join to form one or more substituted or unsubstituted rings.

In a preferred embodiment, the second linkage compound has the structure shown in structure 2, except that at least one of $R^2$ and $R^3$ is $—(Z)_z-C≡CR^E$.

Examples of the second linkage compound of the present method that have an alkyne substituent group are shown below in Table 2.

TABLE 2

Examples of second linkage compound having an alkyne group.

1. phenylacetylene (1-ethynylbenzene),
2. 4-xylyl-1-ethynylbenzene,
3. 4-trifluoromethyl-1-ethynylbenzene,
4. 4-methoxy-1-ethynylbenzene,
5. 4-amino-1-ethylnylbenzene,
6. 5-ethynylpyridine,
7. 4-pentyl-1-ethynylbenzene,
8. 4-phenyl-1-ethynylbenzene,
9. 4-hydroxymethyl-1-ethynylbenzene,
10. 2-methyl-1-ethynylbenzene,
11. 2-fluoro-1-ethynylbenzene,
12. 2-bromo-1-ethynylbenzene,
13. 2-chloro-1-ethynylbenzene,
14. 2,4-difluoro-1-ethynylbenzene,
15. 3-fluoro-1-ethynylbenzene,
16. 3-trifluoromethyl-1-ethynylbenzene,
17. 3-amino-1-ethynylbenzene,
18. 1-ethynylnaphthalene (naphthylacetylene),
19. 3-methoxy-1-ethynylbenzene,
20. 2-ethynyl-4-hydroxy-butylene,
21. 2-ethynyl-2-propanol,
22. 2-ethynyl-propylene,
23. 3-carboxypropylcarbonylamino-1-ethynylbenzene,
24. 4-carboxypropylcarbonylamino-1-ethynylbenzene.

In the preferred second linkage compound that is described in structure 2, the group $L^B$ is termed a linking group. The linking group is chemically linked to the second linkage compound and has at least one reactive group that is free for chemical reaction with another material, such as a biomolecule. Typically, $L^B$ is an organic substituent group which has at least one reactive group that is selected from carboxylic acid esters, sulfonyl halide, acyl halide, aldehydes, reactive ketones, aromatic halides, bromoacetamides, idoacetamides, maleimides, disulfides, hydroxyl, amines, diazonium compounds, active alkylating reagents, active acylating reagents, or diketones. It is preferred that the $L^B$ group is an organic substituent group that is selected from branched or unbranched $C_1$-$C_{12}$ alkyl, $C_1$-$C_{12}$ alkenyl, $C_1$-$C_{12}$ alkynyl, or aryl, heteroaryl, or heterocyclyl, and which has at least one substituent reactive group that is selected from carboxylic acid esters, sulfonyl halide, acyl halide, aldehydes, reactive ketones, aromatic halides, bromoacetamides, idoacetamides, maleimides, disulfides, hydroxyl, amines, diazonium compounds, active alkylating reagents, active acylating reagents, or diketones.

In an alternate embodiment, the second linkage group is one wherein at least one of $R^2$ and $R^3$ is $—(Z)_z—C≡N$. When the second linkage group has a cyano reactive group, rather than an alkyne group, the linkage complex that is formed will be a tetrazole, rather than a triazole. However, the method of using second linkage compounds having cyano reactive groups is the same as for using second linkage compounds having terminal alkyne groups.

In an embodiment of the present method, the second linkage compound is chemically bonded to a biomaterial. The biomaterial can be selected from small molecules (such as, for example, drugs, ligands and catalysts), or from peptides, proteins, nucleic acids, oligonucleotides, saccharides, viruses, cells, organic polymers, inorganic polymers, nanoparticles, or solid surfaces, and the like.

In a manner similar to the first linkage compound discussed above, when the E group of the second linkage compound is a fluorophore, it is preferred that the A group of the first linkage compound is not a fluorophore. In this situation, it is preferred that A is selected from hydrogen, hydroxyl, carboxyl, amino, alkylamino, or a substituted or unsubstituted alkyl, alkenyl, alkynyl, alkoxyl, alkoxyalkyl, alkoxyalkenyl, carboxyalkyl, amino, aminoalkyl, aryl, heteroaryl, or heterocyclyl, and if substituted, at least one substituent is optionally $L^A$, where $L^A$ is a linking group.

As mentioned briefly above, one application of the present invention is to promote and/or measure the conjugation of various biomolecules. In the scheme shown below in equation 2, linkage compounds having azido and terminal alkyne groups react to form a complex having a triazole linkage.

Equation 2:

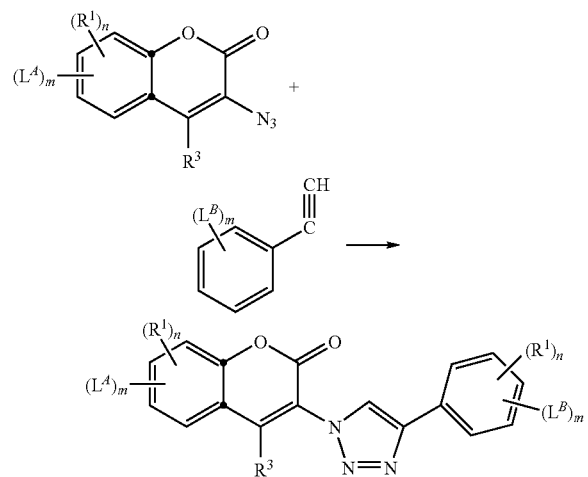

Each of the linkage compounds can have a linking group ($L^A$ and $L^B$) as a substituent group. The properties of the linking groups $L^A$ and $L^B$ has been described above.

Figure 3:
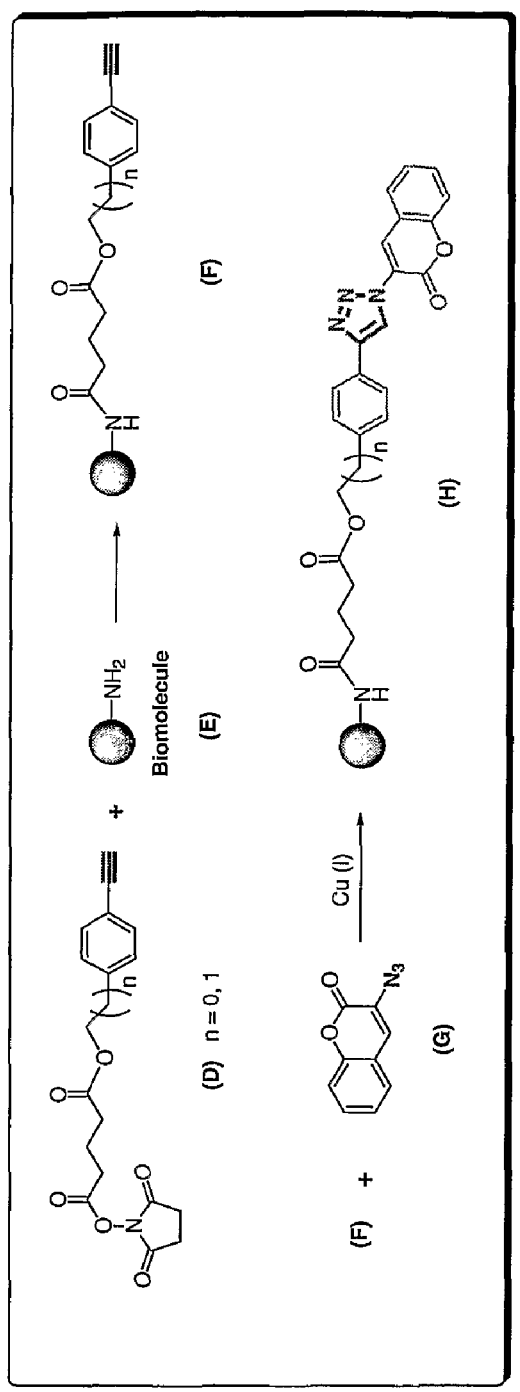
FIG. 3 is an illustration of the reaction of a first linkage compound having an azido reactive group with a second linkage compound having an alkyne group, where the second linkage compound is linked to a biomolecule having a free amino group, such as a protein.

To demonstrate the utility of this technology, several practical examples of conjugation reactions with protein and protein cages (such as are present in viruses) can be shown. As shown in FIG. 3, non-fluorescent linkage compounds D (a second linkage compound) and G (a first linkage compound) can be readily synthesized according to methods that are described herein. The N-succinimide ester group of D is a linking group ($L^B$) that can form an amide bond with any protein at the N-termini of the protein or the amino group of lysine residues. Structure F is a schematic representative of the second linkage compound linked to a protein, for example, through an amide linkage. With catalysis by copper (I) at room temperature or 4° C., F will react with the first linkage compound G to form a new triazolo-complex H, which affords very intense fluorescence emission at 440 nm under irradiation at 376 nm.

In the scheme shown in FIG. 3, the biomolecule, which is represented as a grey ball, can include Cowpea Mosaic Virus (CPMV), Turnips Yellow Mosaic Virus (TYMV), Horse Spleen Ferritin (HSF), BSA, Epidermal Growth Factor Receptor (EGFR), and the like. Additional examples of biological compounds that can be tagged with the novel fluorogenic molecular linkers of the present invention include proteins and protein complexes, such as monoclonal antibody anti-Her-2 protein. In all situations, the present novel conjugation technique shows very high ligation efficiency. The ligated complexes give distinct fluorescent emissions while the starting components (for example, F and G in FIG. 3) are fluorescent inactive. The conjugation yield can be monitored quantitatively via the fluorescent emission spectra, which are consistent with the other calorimetric methods. Furthermore, the conjugated molecules will maintain their original biological activities, which shows the biocompatibility of the present fluorogenic linkers.

Figure 4:
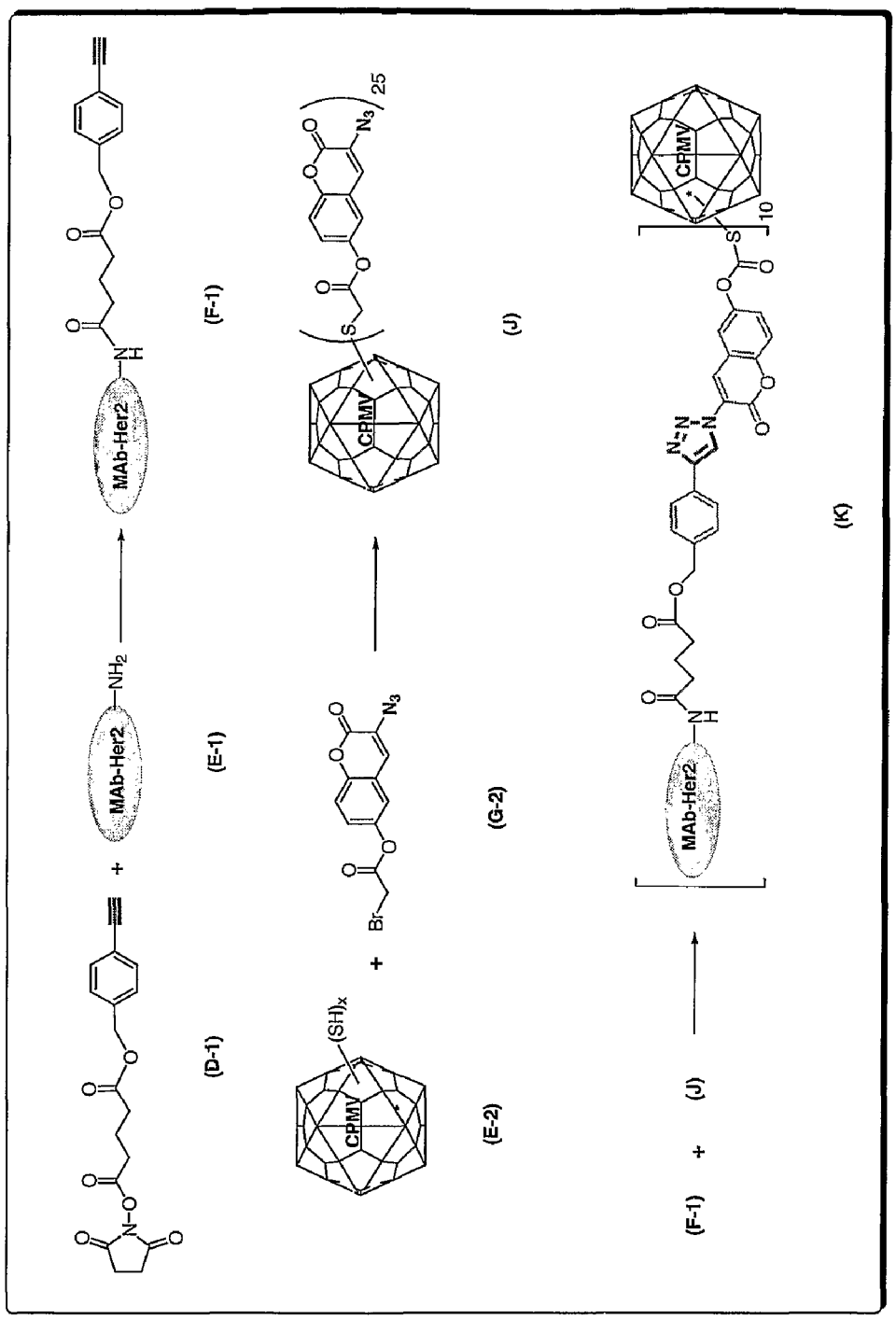
FIG. 4 illustrates an application of an embodiment of the present invention in which a second linkage group (D-1) is linked to a biomolecule (Mab-Her2), while a first linkage group (G-2) is linked to Cowpea Mosaic Virus (CPMV), although neither the F-1 or J compounds are fluorescent, the linkage complex (K) formed by the conjugation of the reactants, shows a strong fluorescent signal.

To further demonstrate the versatility of the present method, another experiment was designed as shown in FIG. 4. In the process of developing new drug delivery systems based on plant viral particles, it is desirable to attach the monoclonal antibody anti-Her2 protein (MAb-Her2) to CPMV. It is very important to know the amount of the antibodies that attach to the viral particles. As illustrated in FIG. 4, the alkyne-modified MAb-Her2 (F-1) and 3-azidocoumarin modified CPMV (J) was first prepared with reagent G-2. With copper (I) as catalyst, F-1 reacted with J to afford the antibody-CPMV complex K. The fluorescence emission of K was used to calculate the stoichiometry.

Similarly, either first or second linkage compounds can be attached to supramolecular assemblies such as whole cells in order to create sites on the cell wall at which a compatible linkage group can attach to form a linkage complex that includes the cell. That cell will then show a distinct fluorescent signal. This procedure is useful when it is desirable to detect cellular species of particular interest. Because the components of the present system—azides, acetylenes and coumarins are biocompatible, the present method can be employed to monitor the conjugation yield in biological systems—even in intact living systems.

An additional feature of the present invention is that by selection of the chemical composition of the two linkage compounds, one can select the optical properties (such as the peak fluorescence wavelength) that are most desirable and useful for a particular application. By way of example, when one reacts 3-azidocoumarin with phenylacetylene, the triazole product shows intense blue fluorescence at 478 nm, when radiated at a wavelength of 340 nm. However, the reaction of 4-azidocoumarin with phenylacetylene gives a product that, while chemically very similar, shows no fluorescence at all. This result shows that the location of the azide group on the coumarin affects the fluorogenic property of the linkage complex.

It is obvious that the structure of the linkage compounds have a great impact on the fluorescent properties of the linkage complex. In general, fluorescent emission in the UV region is observed if aliphatic alkynes are used as starting materials. Non-fluorescent linkage complexes are obtained if phenylacetylene with electron donating groups are used as starting materials. Surprisingly, para-alkyl substitution stimulated the fluorescence of the triazolyl linkage complex.

Due to mild reaction conditions, it is easy to synthesize many triazolyl dyes in a combinatorial manner. In fact, many of the substituted and unsubstituted 3-azidocoumarin and 4-azidocoumarin compounds of Table 1 were reacted with many of the alkyne compounds shown in Table 2. The reactions were carried out for 12 hours in the presence copper sulfate and sodium ascorbate in DMSO/water solution at room temperature. Table 3, shows the excitation wavelength ($\lambda$ex) and the emission wavelength $\lambda$em of the linkage complex products of the 192 combinations.

TABLE 3

Fluorescence data of triazolyl coumarin linkage complex products.

| Code | λex (nm) | λem (nm) | Code | λex (nm) | λem (nm) | Code | λex (nm) | λem (nm) | Code | λex (nm) | λem (nm) |
|---|---|---|---|---|---|---|---|---|---|---|---|
| A1 | 340 | 478 | B1 | 441 | 494 | C1 | 350 | 430 | D1 | 443 | 495 |
| A2 | 341 | 507 | B2 | 441 | 495 | C2 | 353 | 443 | D2 | 440 | 494 |
| A3 | 346 | 405 | B3 | 444 | 495 | C3 | 350 | 426 | D3 | 442 | 495 |
| A4 | 0 | 0 | B4 | 445 | 495 | C4 | 0 | 0 | D4 | 440 | 495 |
| A5 | 0 | 0 | B5 | 442 | 497 | C5 | 0 | 0 | D5 | 444 | 497 |
| A6 | 342 | 406 | B6 | 442 | 494 | C6 | 350 | 425 | D6 | 444 | 495 |
| A7 | 341 | 504 | B7 | 443 | 495 | C7 | 353 | 444 | D7 | 441 | 495 |
| A8 | 342 | 515 | B8 | 444 | 496 | C8 | 353 | 473 | D8 | 441 | 495 |
| A9 | 353 | 473 | B9 | 441 | 495 | C9 | 352 | 429 | D9 | 443 | 495 |
| A10 | 338 | 485 | B10 | 443 | 494 | C10 | 351 | 430 | D10 | 440 | 494 |
| A11 | 0 | 0 | B11 | 444 | 495 | C11 | 351 | 426 | D11 | 440 | 494 |
| A12 | 348 | 403 | B12 | 444 | 494 | C12 | 351 | 425 | D12 | 441 | 494 |
| A13 | 342 | 425 | B13 | 442 | 494 | C13 | 350 | 426 | D13 | 444 | 494 |
| A14 | 0 | 0 | B14 | 444 | 495 | C14 | 350 | 426 | D14 | 441 | 494 |
| A15 | 0 | 0 | B15 | 444 | 495 | C15 | 351 | 427 | D15 | 441 | 494 |
| A16 | 343 | 427 | B16 | 445 | 495 | C16 | 351 | 426 | D16 | 442 | 495 |
| A17 | 0 | 0 | B17 | 444 | 495 | C17 | 0 | 0 | D17 | 441 | 495 |
| A18 | 0 | 0 | B18 | 440 | 494 | C18 | 351 | 507 | D18 | 439 | 494 |
| A19 | 0 | 0 | B19 | 444 | 495 | C19 | 351 | 432 | D19 | 441 | 494 |
| A20 | 303 | 388 | B20 | 440 | 494 | C20 | 349 | 420 | D20 | 442 | 494 |
| A21 | 339 | 400 | B21 | 440 | 492 | C21 | 348 | 421 | D21 | 442 | 492 |
| A22 | 348 | 390 | B22 | 440 | 493 | C22 | 350 | 421 | D22 | 442 | 494 |
| A23 | 0 | 0 | B23 | 441 | 495 | C23 | 0 | 0 | D23 | 443 | 496 |
| A24 | 0 | 0 | B24 | 442 | 495 | C24 | 0 | 0 | D24 | 443 | 495 |
| E1 | 417 | 489 | F1 | 435 | 508 | G1 | 348 | 501 | H1 | 307 | 429 |
| E2 | 417 | 489 | F2 | 434 | 508 | G2 | 348 | 521 | H2 | 333 | 497 |
| E3 | 417 | 489 | F3 | 435 | 509 | G3 | 348 | 410 | H3 | 306 | 415 |
| E4 | 418 | 489 | F4 | 435 | 508 | G4 | 347 | 408 | H4 | 310 | 408 |
| E5 | 415 | 488 | F5 | 433 | 507 | G5 | 0 | 0 | H5 | 0 | 0 |
| E6 | 417 | 489 | F6 | 435 | 508 | G6 | 346 | 406 | H6 | 312 | 451 |
| E7 | 417 | 489 | F7 | 435 | 508 | G7 | 349 | 520 | H7 | 310 | 408 |
| E8 | 416 | 489 | F8 | 435 | 508 | G8 | 353 | 518 | H8 | 298 | 512 |
| E9 | 417 | 488 | F9 | 435 | 507 | G9 | 348 | 499 | H9 | 309 | 448 |
| E10 | 416 | 488 | F10 | 433 | 507 | G10 | 346 | 506 | H10 | 310 | 420 |
| E11 | 416 | 489 | F11 | 435 | 507 | G11 | 343 | 405 | H11 | 307 | 414 |
| E12 | 417 | 489 | F12 | 435 | 508 | G12 | 349 | 412 | H12 | 308 | 421 |
| E13 | 416 | 489 | F13 | 434 | 508 | G13 | 346 | 410 | H13 | 307 | 413 |
| E14 | 417 | 489 | F14 | 435 | 509 | G14 | 354 | 395 | H14 | 309 | 414 |
| E15 | 417 | 489 | F15 | 435 | 508 | G15 | 0 | 0 | H15 | 308 | 418 |
| E16 | 418 | 489 | F16 | 436 | 508 | G16 | 0 | 0 | H16 | 307 | 416 |
| E17 | 416 | 488 | F17 | 435 | 507 | G17 | 325 | 380 | H17 | 0 | 0 |
| E18 | 416 | 489 | F18 | 434 | 508 | G18 | 0 | 0 | H18 | 0 | 0 |
| E19 | 417 | 489 | F19 | 435 | 507 | G19 | 353 | 413 | H19 | 307 | 415 |
| E20 | 415 | 488 | F20 | 434 | 507 | G20 | 355 | 397 | H20 | 310 | 409 |
| E21 | 413 | 484 | F21 | 431 | 503 | G21 | 358 | 416 | H21 | 310 | 446 |
| E22 | 415 | 486 | F22 | 433 | 506 | G22 | 359 | 418 | H22 | 309 | 411 |
| E23 | 416 | 488 | F23 | 433 | 507 | G23 | 355 | 397 | H23 | 308 | 412 |
| E24 | 417 | 488 | F24 | 435 | 507 | G24 | 353 | 395 | H24 | 307 | 413 |

Notes:
"Code" indicates the linkage compounds used in the combination to form a linkage complex, where the first letter identifies the first linkage compound according to the listing of Table 1, and the following numerals identifies the second linkage compound according to the listing of Table 2.
λex is the maximum excitation wavelength in nanometers.
λem is the maximum emission wavelength in nanometers.

Figure 5:
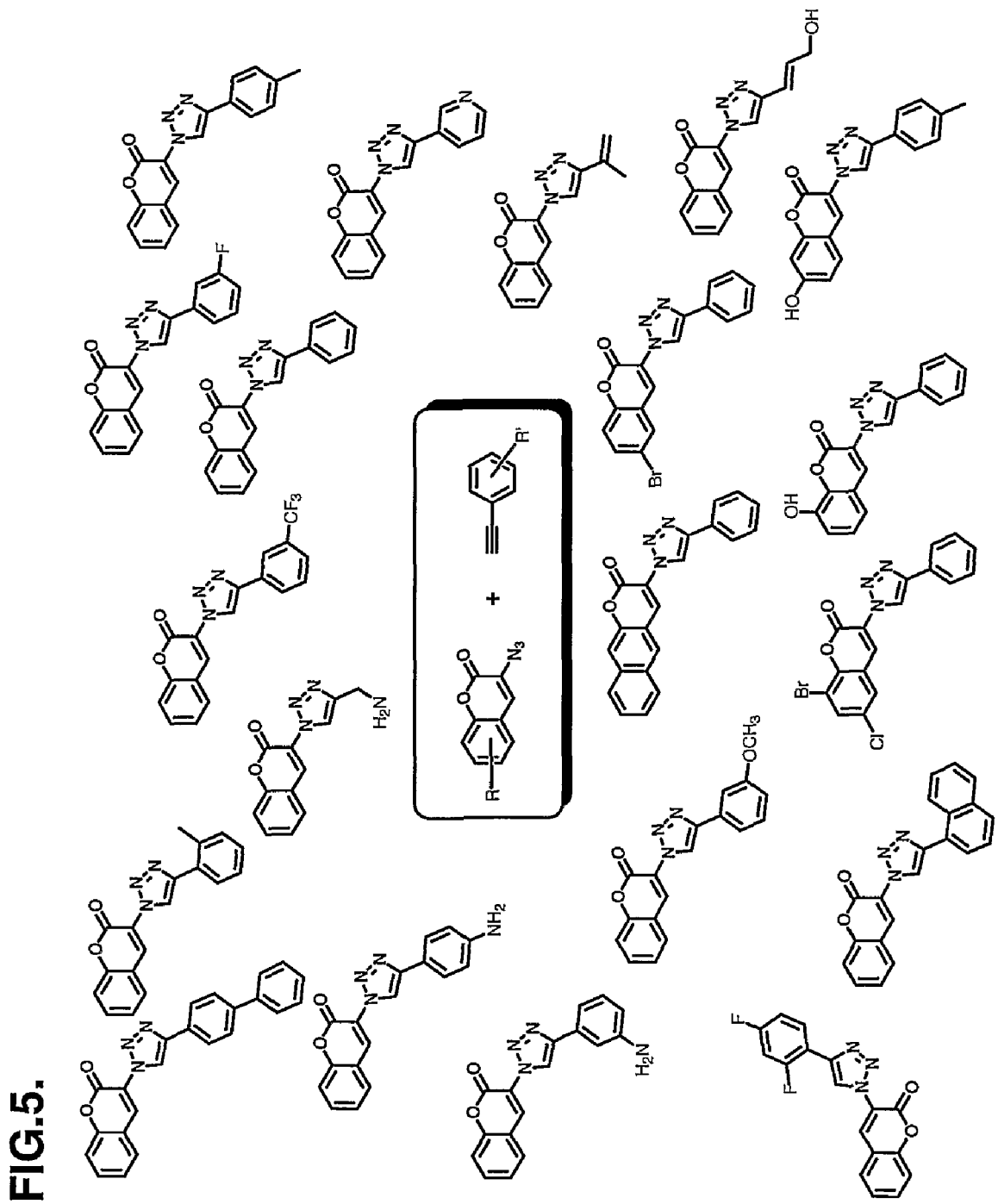
FIG. 5 illustrates examples of triazolyl linkage complexes that can be formed by reacting substituted and unsubstituted coumarin having an azido reactive group with a first linkage compound having an azido alkyne reactive group

In fact, from commercially available starting materials, one can easily generate thousands of different fluorescent dyes with varied optical properties. Some examples of linkage complexes are shown in FIG. 5.

The present method shows excellent flexibility as to the selection of desirable optical properties for the fluorescent signal of the linkage complex. For example, the selection of suitable linkage compounds permit the control of: (1) the wavelength of maximum absorption; (2) the wavelength of the maximum emission; (3) the absorption intensity or extinction coefficient, $\epsilon$, which reflects the probability of absorption; (4) the quantum yield, $\phi$, which is the characteristic of the emission intensity of a fluorochrome; (5) the fluorescence life time or excited lifetime, $\tau$, which is the average time that a molecule remains in the excited state; and (6) the photostability.

As discussed above, the present method is used for bioconjugation. Ideally, the dyes that can be used as fluorescent probes for biological activity should have high quantum yield (>0.4), short fluorescence life time and high photostability. Special wavelength may be required for different applications. For in vivo probing, the interference from the native fluorescence of cytoplasmic flavins, flavoproteins and NADPH should be considered and avoided. For bioconjugation, it is also very important to measure the difference of emission wavelength and emission intensity between the triazole product and the starting materials.

One major application of the novel method is to probe the bioconjugation in situ. By way of example, because Cowpea Mosaic Virus (CPMV) has already been demonstrated as a robust scaffold for organic reactions, it can be employed as a bio-platform. See, e.g., Wang, Q. et al., *Chemistry and Biology*, 9:813-819 (2002); Wang, Q. et al. *Chemistry and Biology* 9: 805-812 (2002); and Wang, Q. et al., *Angew. Chem. Int. Ed.*, 41(3): 459-462 (2002).

Figure 6:
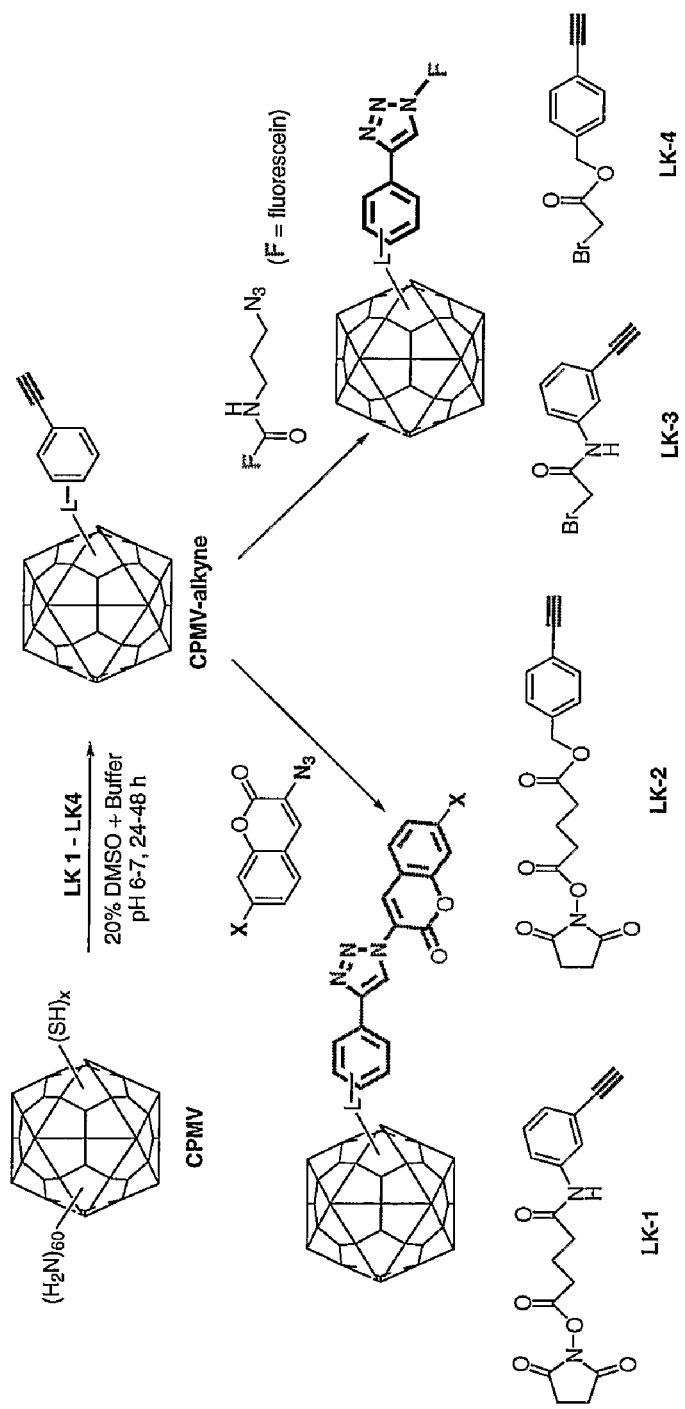
FIG. 6 illustrates an example of how an embodiment of the present method can be used to link any material of interest ("X") to a virus particle (here, "CPMV") to provide a fluorescent linkage complex.

As shown in FIG. 6, linkage compounds (LK-1 to LK-4, for example) can be used to modify CPMV at either the reactive lysine residues or cysteine residues. The alkyne groups on CPMV can be reacted with fluorescein-azide. As an alternative, the virus can be reacted with an azidocoumarin linkage compound. Small coumarin reagents can be employed in the reaction, or the coumarin-azide will be attached to other biomolecules, e.g. proteins, DNA, virus, and cells, which will be ligated to CPMV. Similarly, coumarin-azide can be attached to CPMV before it reacts with an alkyne counterpart. In all the cases, the ligated complexes give distinct fluorescent emission while the starting components are fluorescent inactive.

An advantage of the present invention is that it permits the biosystem to maintain the original biological properties after the conjugation. One can easily select the best combination of azide and alkyne prelinkers for each application.

Other types of azide based reactions are also useful in the present method. One example that has been discussed briefly above is the use of second linkage compound having a cyano reactive group, rather than an alkyne group. When a second linkage compound having a cyano group is reacted with, for example, a first linkage compound having an azido reactive group, the linkage complex includes a tetrazole group, rather than a triazole. This is illustrated in equation 3, below, where the transformation from cyano to tetrazole changes the emission wavelength dramatically. For example, when $L^B$ is diethylamino, the unreacted second linkage group has orange fluorescence, while, after reaction, the tetrazole linkage complex has greenish yellow fluorescence.

Equation 3:

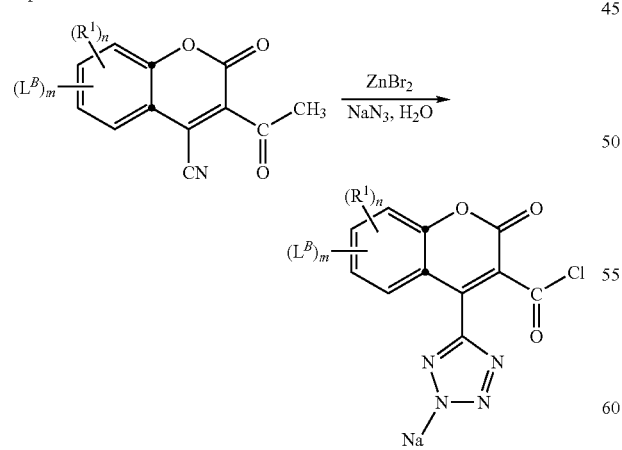

This transformation together with azide-acetylene cycloaddition opens many possibilities for modifying and controlling the optical properties of linkage complexes. Some examples include those shown in equation 4, below:

Equation 4:

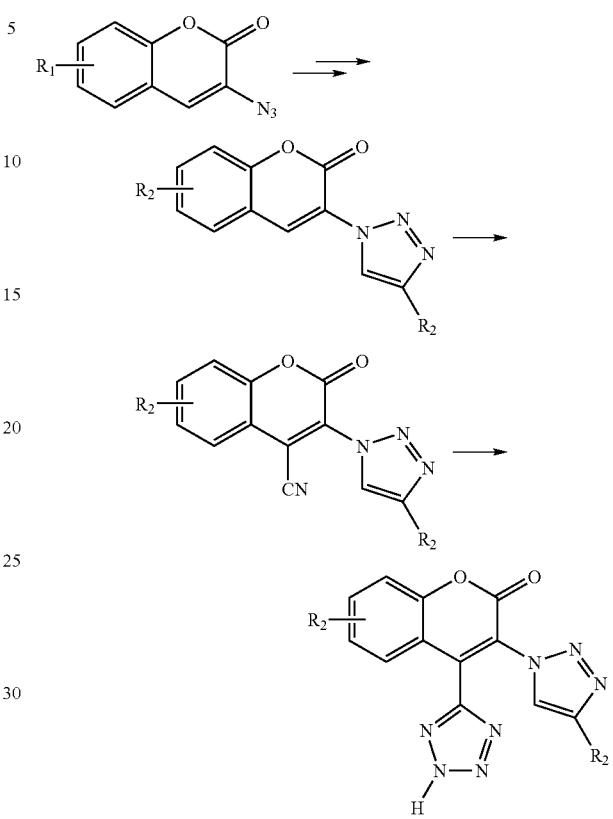

When starting with a fluorophore such as juloridine, the products will have many industrial applications such as laser dyes. Some of the linkage complexes that are useful include those shown below:

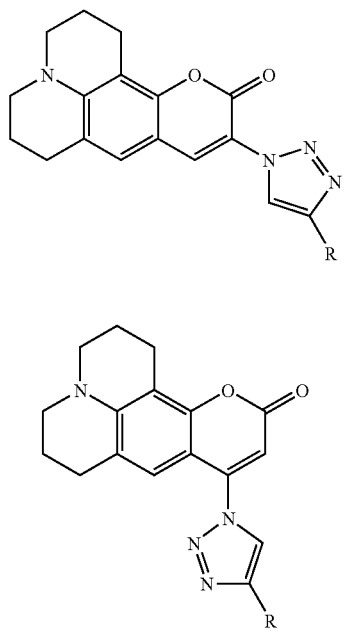

-continued

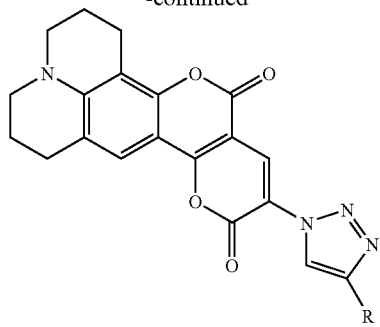

Other useful fluorescent linkage groups include the following ethynyl substituted coumarins:

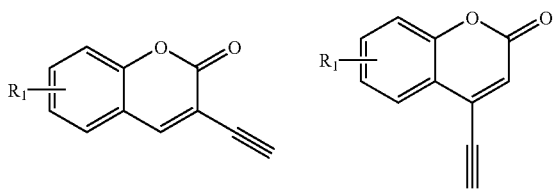

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

General Procedures

Chemicals used in the synthesis methods described herein can be purchased commercially (for example, from Sigma-Aldrich, St. Louis, Mo., or Acros Organics, Geel, Belgium) and can be used without further purification.

Melting points were uncorrected.

NMR spectra were recorded with a Varian Mercury/VX 300 spectrometer and the delta ($\delta$) values are in ppm vs. $SiMe_4$ (0 ppm, $^1H$, 300 MHz).

IR spectra were recorded with a Shimadzu FTIR Spectrophotometer.

Mass spectra were recorded using a Micromass O-T of I mass spectrometer.

Fluorescence emission and excitation spectra were recorded using a JASCO FP-6500 Spectrofluorometer.

Quantum yields were determined in THF using 9,10-diphenylanthracene as the fluorescence standard. The path length was 1 cm with a cell volume of 3.0 ml.

The synthesis of azidocoumarins generally followed the procedure of Tripathy et al., *Indian J. Chem., Section E: Org. Chem. Including Med. Chem.*, 26B:61-62 (1987), and Higuchi et al., *Heterocycles*, 35:937-947 (1993), Higuchi, Y. et al. *Heterocycles*, 35:937-947 (1993), Chaurasia, C. S. et al. *Heterocyclic Chem.*, 27: 727-733 (1990), Oh, C. S. et al., *Heterocyclic Chem.*, 31:841-844. (1994), and Ito, K., and Hariya, J.; *Heterocycles*, 26: 35-38 (1987).

Synthesis of Starting Materials

A. Synthesis of 3-azidocoumarin

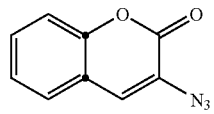

3-Aminocoumarin (250 mg, 1.6 mmol) was dissolved in 30 mL of 3% HCl at room temperature. After cooling to 0-5° C., the solution was added drop-wise to a solution of $NaNO_2$ (160 mg, 2.3 mmol) and stirred for two hours. Upon addition of $NaN_3$ (150 mg, 2.3 mmol), the mixture was stirred at 0-5° C. for two hours followed by stirring at room temperature for three and a half hours. The precipitate was filtered, washed to neutral pH with water and dried under vacuum to afford a white solid; yield (226 mg, 78%); mp: 108-112° C.; $^1H$-NMR (300 MHz, $CDCl_3$): $\delta$ 7.2-7.6 (m, 5H).

E. Synthesis of 3-Azido-7-diethylaminocoumarin

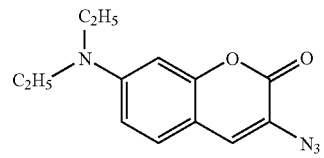

Following the procedure described in Procedure A, but starting from 3-amino-7-diethylaminocoumarin, 89 mg of a yellow solid was obtained (80.04%). $^1H$ NMR (300 MHz, $CDCl_3$): $\delta$1.26 (t, 6H), 3.48 (q, 4H), 6.50 (s, 1H), 6.70 (d, 1H), 7.10 (s, 1H), 7.20 (d, 1H).

C. Synthesis of 4-azidocoumarin

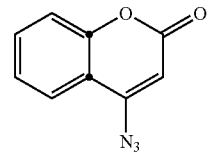

4-chloro coumarin, (100 mg, 0.54 mmol) was dissolved in 2 mL of DMF at room temperature and followed by the addition of $NaN_3$ (40 mg, 0.62 mmol) and stirring for twelve hours. The reaction mixture was poured onto 10 g of ice, and then stirred for 30 minutes at room temperature. Filtration and drying afforded white powder; yield (80 mg, 80%); mp 159-160° C. $^1H$-NMR (300 MHz, $CDCl_3$): $\delta$ 7.2-7.7 (m, 5H).

D. Synthesis of 3-azido-7-hydroxycoumarin

A mixture of 2,4-dihydroxy benzaldehyde (2.76 g, 20 mmol), N-acetylglycine (2.34 g, 20 mmol), anhydrous sodium acetate (60 mmol) in acetic anhydride (100 ml) was refluxed under stirring for 4 hours. The reaction mixture was poured onto icde to give a yellow precipitate. After filtration, the yellow solid washed with ice water before it was refluxed in a solution of concentrated HCl and ethanol (2:1, 30 ml) for 1 hour, then ice water was added to dilute the solution. The solution was then cooled in an ice bath and NaNO$_2$ (40 mmol) was added. The mixture was stirred for 5-10 minutes and NaN$_3$ (60 mmol) was added in portions. After stirring for another 15 minutes, the resulting precipitate was filtered off, washed with water, and dried under reduced pressure to afford a brown solid: 2.2 g (54% overall yield). The product was pure enough for further reactions. $^1$H NMR (DMSO-d$_6$, 300 MHz) δ 6.74 (d, J=2.2 Hz, 1H), 6.79 (dd, J=8.4. 2.2 Hz, 1H), 7.47 (d, J=8.5 Hz, 1H), 7.56 (s, 1H). $^{13}$C NMR (DMSO-d$_6$, 75 MHz) δ 161.0, 158.0, 153.4, 128.7, 128.5, 121.8, 114.5, 112.0, 102.7. IR (KBr): 3296 (s), 2125 (vs), 1680 (s), 1620 (m), 1321 (s). EI-HRMS m/e calculated for M$^+$ C$_9$H$_5$N$_3$O$_3$ 203.0331; found 203.0326.

E. Synthesis of 3-Azido-7-methoxychromen-2-one (3-Azido-7-Methoxycoumarin)

In dry acetone (20 mL), 3-azido-7-hydroxycoumarin (203 mg, 1.0 mmol), anhydrous K$_2$CO$_3$ (250 mg), CH$_3$I (0.13 mL, 200 mg, 1.4 mmol) was refluxed overnight. After filtration, acetone was removed using a rotary evaporator, and the residue was dissolved with ethyl acetate (50 mL). The organic layer was dried over anhydrous Na$_2$SO$_4$ and concentrated under reduced pressure providing the product as a yellow solid; 185 mg, 81%; $^1$H-NMR (DMSO-d6, 300 MHz) δ 3.81 (s, 3H), 6.95 (dd, J=9.0, 2.7 Hz, 1H), 7.03 (d, J=2.7, 1H), 7.56 (d, J=9.5, 1H), 7.62 (s, 1H). $^{13}$C NMR (DMSO-d6, 75 MHz) δ 56.6, 101.3, 113.2, 113.7, 122.8, 128.0, 129.5, 153.3, 157.9, 162.2. IR (KBr): 3406 (vs), 2125 (vs), 1616 (s), 1155 (m). EI-HRMS m/e calculated for M+ C$_{10}$H$_7$N$_3$O$_3$ 217.0487; found 217.0469.

F. Synthesis of acetic acid 3-azido-2-oxo-2H-chromen-7-yl ester (7-Acetic-3-azidocoumarin)

To a stirred suspension of 3-azido-7-hydroxycoumarin (203 mg, 1.0 mmol) in dry CH$_2$Cl$_2$ (15 mL), acetic anhydride (1.5 mmol) and pyridine (one drop) were added. Upon stirring overnight at room temperature, the solvent was removed under reduced pressure. The residue was dissolved in ethyl acetate and washed with H$_2$O. The organic layer was dried over anhydrous Na$_2$SO$_4$ and concentrated. Purification with column chromatography over silica gel (hexane-EtOAc 4:1) afforded the final product as a yellow solid (210 mg, 86%). $^1$H-NMR (DMSO-d6, 300 MHz) δ 2.29 (s, 3H), 7.17 (dd, J=8.0, 2.0 Hz, 1H), 7.32 (d, J=2.1 Hz, 1H), 7.67 (s, 1H), 7.70 (d, J=7.9 Hz, 1H). $^{13}$C NMR (DMSO-d6, 75 MHz) δ 21.5, 110.6, 117.8, 119.9, 125.8, 126.8, 129.2, 151.9, 152.3, 157.5, 169.6. IR (KBr): 2133 (vs), 1749, 1730 (vs), 1622 (s), 1234 (s). EI-HRMS m/e calculated for M+ C$_{11}$H$_7$N$_3$O$_4$ 245.0437; found 245.0432.

G. Synthesis of 3-Azido-7-diethylaminochromen-2-one (3-azido-7-diethylaminocoumarin)

A mixture containing n-butanol (20 mL), 4-diethylamino salicylaldehyde (1.4 g, 7.2 mmol), ethyl nitroacetate (0.8 mL, 7.2 mmol), molecular sieves 4 Å (100 mg), piperidine (0.1 mL) and acetic acid (0.2 mL) was refluxed for a period of 24 h. Upon cooling to room temperature, a bright yellow solid formed, which was collected and dissolved in DMF (15 mL) at 80° C. It was filtered again to remove the molecular sieves. The filtrate, upon addition to 100 ml of ice-cold water, yielded 3-nitro-7-diethylamino coumarin as a bright yellow solid: 1.40 g, 73%. A small amount of this compound was recrystallized from DMF to give an analytical sample; mp 193-195° C. $^1$H-NMR (CDCl3, 300 MHz) δ 1.27 (t, J=7.14 Hz, 6H), 3.48 (q, J=7.86 Hz, 4H), 6.50 (s, 1H), 6.70 (d, J=6.71 Hz, 1H), 7.42 (d, J=7.42 Hz, 2H), 8.72 (s, 1H). HRMS m/e calculated for MH$^+$ C$_{13}$H$_{14}$N$_2$O$_4$ 263.1041; found 263.1032.

In a 25 mL round bottomed flask equipped with a magnetic stirrer, were placed in order, 37.4% HCl (5 mL), stannous chloride dihydrate (1.6 g, 7.12 mmol). To this suspension 3-nitro-7-diethylamino coumarin (0.25 g, 0.95 mmol) was added at room temperature in small portions, over a period of thirty minutes. Stirring was continued for 4 h before the solution was poured onto 20 g of ice and made alkaline using sodium hydroxide solution (5 M) at 15° C. using an ice-water bath. The resulting suspension was then extracted with diethyl ether (2×25 mL). The organic layer washed with water (50 mL), dried over anhydrous sodium sulfate and concentrated to a pasty residue which upon triturating using hexane yielded 3-amino-7-diethylaminocoumarin as a pale yellow solid: 0.15 g, 68%. A small amount of this compound was recrystallized in ethyl acetate/hexane to give an analytical sample; mp 85-87° C. IR (KBr): 3323, 3398 (m), 1697 (m), 1589 (m), 1517 (m). $^1$H NMR (CDCl3, 300 MHz) δ 1.27 (t, J=7.17 Hz, 6H), 3.48 (q, J=7.22 Hz, 4H), 3.85 (s, 2H), 6.6 (m, 2H), 6.7 (s, 1H), 7.10 (d, J=8.65 Hz, 1H). HRMS m/e calculated for MH$^+$ C$_{13}$H$_{16}$N$_2$O$_2$ 233.1282; found 233.1290.

7-Diethylamino-3-amino coumarin (100 mg, 0.43 mmol) was dissolved slowly in HCl aq. (17.2%, 4 mL) at room temperature. Upon cooling to 0-5° C. and addition of a solution of NaNO$_2$ (30 mg, 0.43 mmol), the reaction mixture was stirred for 1 hour at 0-5° C. This was followed by the addition of potassium acetate (2 g) in water (5 mL) to adjust the pH of the resulting solution to 4. Sodium azide (57 mg, 0.88 mmol) was added in portions at 0-5° C., the mixture stirred at 0-5° C. for another five hours. The precipitated product was rapidly filtered, washed with ice-cold water (10 mL) and dried under vacuum to yield the final product as a yellow solid: 84 mg, 80%. The product was stored at −20° C. IR (KBr): 2113 (vs), 1710 (s), 1625 (m), 1512 (m); $^1$H NMR (300 MHz, CDCl$_3$) δ 1.26 (t, J=7.25 Hz, 6H), 3.48 (q, J=7.24 Hz, 4H), 6.50 (s, 1H), 6.70 (d, J=8.04 Hz, 1H), 7.10 (s, 1H), 7.20 (d, J=9.07 Hz, 1H); EI-MS for C$_{13}$H$_{14}$N$_4$O$_2$ m/z (MH+): 259.

H. Synthesis of 9-Azido-2,3,5,6-tetrahydro-1H,4H-11-oxa-3a-aza-benzo[de]anthracen-10-one 10-Amino-2,3,6,7-tetrahydro-11-oxo-1H-benzo[b]pyrano-[6,7,8-i,j]isoquinolizine (200 mg, 0.78 mmol) was dissolved slowly in 2 ml of 17.2% HCl at room temperature. After cooling to 0-5° C., a solution of NaNO$_2$ (64 mg, 0.93 mmol) was added drop-wise to the mixture, which was stirred for one hour at 0-5° C. This was followed by dilution of the reaction using 25 ml of ice cold water and stirring continued for thirty minutes at 0-5° C. Maintaining the same temperature, sodium azide (130 mg, 0.88 mmol) was added in portions and the mixture stirred for fifteen minutes. The pH of the resulting solution was adjusted to 4 by the addition of saturated potassium acetate solution in water and the stirring continued another five hours. The precipitated product was rapidly filtered, washed with 20 ml of ice-cold water and dried under vacuum to yield 180 mg of the product as a greenish yellow solid (82% yield). The product was stored at −20° C. IR (KBr): 2113 (vs), 1701 (s), 1625 (m), 1512 (m); $^1$H NMR (300 MHz, CDCl$_3$) δ 1.84-1.89 (m, 4H), 2.64-2.70 (m, 4H), 3.23 (m, 4H), 6.96 (s, 1H), 7.39 (s, 1H); EI MS for $C_{15}H_{14}N_4O_2$ m/z (MH+): 283.

I. Synthesis of 3-Azido-6-bromo-chromen-2-one (3-Azido-6-bromocoumarin)

Benzenesulfonyl chloride (4.4 g, 25 mmol) was added into a solution of N-acetylglycine (2.93 g, 25 mmol) and triethylamine (6.3 g, 62.5 mmol) in dry benzene (125 ml). The mixture was stirred at room temperature for 4 h before the triethylamine hydrochloride salt was removed by filtration. To the filtrate, 5-bromosalicylaldehyde (5.0 g, 25 mmol) was added. After refluxing for 2 h, the reaction mixture was cooled to room temperature and the solvents were removed under reduced pressure. The residue was then washed with hot ethanol (100 mL) and the light yellow precipitation was collected as 3-acetamido-6-bromocoumarin. More product could be recovered from the ethanol solution. The overall yield was 3.5 g (52%).

3-Acetamido-6-bromocoumarin (1 g, 3.7 mmol) was dissolved in a mixture of concentrated HCl aq. and ethanol (v/v=2:1, 18 mL) and refluxed for 2 h. After cooling the mixture to room temperature, ice water (10 ml) was poured into the reaction system, which was stirred in an ice bath until the interior temperature was lower than 5° C. Sodium nitrite (621 mg, 9 mmol) was added in portions during 10 min and stirred vigorously for 5 min before $NaN_3$ (720 mg, 11 mmol) was added. The reaction mixture was then stirred in ice bath for one hour at 0-5° C. and 24 h at room temperature. The crude product thus obtained was collected by filtration and purified on silica gel (hexane-EtOAc=4:1) to yield the product as white solid; 320 mg, 33%. IR (KBr): 2133 (vs), 1693 (vs), 1413 (m), 1355 (m). $^1$H NMR (DMSO-d6, 300 MHz) δ 7.10 (s, 1H), 7.21 (d, J=9.5 Hz, 1H), 7.54 (m, 3H). EI-HRMS m/e calculated for (M+) $C_9H_4BrN_3O_2$ 264.9487; found 264.9489.

J. Synthesis of 3-Azido-8-ethoxy-chromen-2-one

The synthesis is analogous to that described in "I", above, but with 6-ethoxysalicylaldehyde as the starting material. The product was obtained as a light yellow solid; 120 mg, 20%. IR (KBr): 3413 (vs), 2125 (vs), 1616 (s), 1467 (m), 1336 (m). $^1$H NMR (DMSO-d6, 300 MHz) δ 1.40 (t, J=6.9 Hz, 3H), 4.17 (q, J=7.0 Hz, 2H), 7.23 (m, 3H), 7.64 (s, 1H). $^{13}$C NMR (DMSO-d6, 75 MHz) δ 15.3, 65.0, 114.5, 119.7, 120.7, 125.8, 126.4, 127.4, 140.9, 146.3, 157.4. EI-HRMS m/e calculated for M+ $C_{11}H_9N_3O_3$ 231.0644; found 231.0640.

K. Synthesis of 4-cyano-3-acetyl-7-diethylaminocoumarin

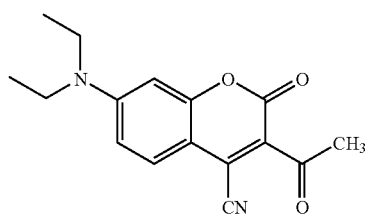

3-acetyl-7-diethylaminocoumarin (259 mg, 1 mmol) was dissolved in 3 mL of DMSO and the resulting solution was stirred at room temperature for 30 minutes. Sodium cyamide (100 mg, 2 mmol) was added and the stirring continued at room temperature for two hours. Iodine (253 mg, 1 mmol) was added into the brown colored solution and stirred for additional two hours at room temperature. The resulting solution was poured drop wise into 20 g of ice and stirred for 30 minutes at room temperature. The product precipitated was then filtered, washed with 20 mL water and dried under vacuum to yield a red solid (232 mg, 82%). $^1$H NMR (300 MHz, CDCl$_3$): δ1.26 (t, 6H), 3.48 (q, 4H), 6.50 (s, 1H), 6.70 (d, 1H), 7.80 (d, 1H).

L. Synthesis of 4-(3-Ethynyl-phenylcarbamoyl)-butyric acid (23)

Glutaric anhydride (215 mg, 1.9 mmol) was dissolved in anhydrous dichloromethane (7 ml) and followed by the addition of 3-ethynylaniline (200 mg, 1.7 mmol). The mixture was allowed to stir at room temperature for 6 hours before the solvent was evaporated under reduced pressure to provide the product as a white solid (363 mg, 99%);

mp 150-154° C.; $^1$H NMR (DMSO-d6, 300 MHz) δ 1.77 (p, J=7.77 Hz, 2H), 2.25 (t, J=8.10 Hz, 2H), 2.33 (t, J=7.13 Hz, 2H), 4.15 (s, 1H), 7.12 (d, J=7.60 Hz, 1H), 7.25 (t, J=7.60 Hz, 1H), 7.51 (d, J=8.29 Hz, 1H), 7.76 (s, 1H), 9.96 (s, 1H); HRMS m/e calculated for (M+H)$^+$ $C_{13}H_{13}NO_3$ 231.0895; found 231.0895.

M. Synthesis of 4-(4-Ethynyl-phenylcarbamoyl)-butyric acid (24)

Glutaric anhydride (540 mg, 4.70 mmol) was dissolved in anhydrous dichloromethane (7 mL) and followed with the addition of p-aminophenyl-acetylene (500 mg, 4.27 mmol). The mixture was allowed to stir at room temperature for 6 hours before the solvent was evaporated under reduced pressure to provide 900 mg of a yellow white product 24 (96%); mp 135-140° C.; $^1$H NMR (DMSO-d6, 300 MHz) δ 1.77 (p, J=8.21 Hz, 2H), 2.25 (t, J=9.30 Hz, 2H), 2.34 (t, J=6.56 Hz, 2H), 4.05 (s, 1H), 7.38 (d, J=8.52 Hz, 2H), 7.59 (d, J=7.91 Hz, 2H) 9.90 (s, 1H); HRMS m/e calculated for (M+H)$^+$: $C_{13}H_{13}NO_3$ 231.0895; found 231.0895.

Example 1

This example illustrates the fluorogenic conjugation of 3-azidocoumarin and phenyl acetylene to form the fluorescent linkage product shown below.

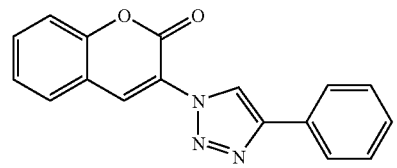

Phenyl acetylene (55 mg, 0.5 mmol) and 3-azidocoumarin (100 mg, 0.5 mmol) were mixed with a 1:1 mixture of water and ethyl alcohol (5 mL). Sodium ascorbate (60 μL, 0.06 mmol of freshly prepared 1 M solution in water) was added, followed by the addition of copper sulfate 7.5% in water (20 μL, 0.06 mmol). The heterogeneous mixture was stirred vigorously overnight, and TLC analysis indicated complete consumption of the reactants. The reaction mixture was diluted with water (5 mL), cooled in ice, and the precipitate was collected by filtration. After washing the precipitate with cold water (10 mL), it was dried under vacuum to afford 90 mg (58%) of pure product as an off-white powder. ¹H NMR (300 MHz, CDCl₃) δ 7.3-7.8 (m, 9H), 8.8 (s, 1H), 9.2 (s, 1H).

Example 2

This example illustrates the conjugation of 4-azidocoumarin and phenyl acetylene to form the linkage product shown below.

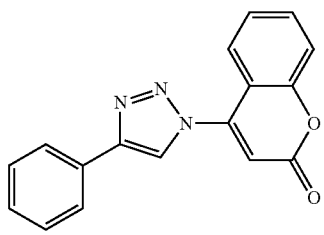

Analogously to the procedure described in Example 4, 4-azidocoumarin was used as starting materials to give pure product as an off-white powder; yield 78%. ¹H-NMR (300 MHz, CDCl₃) δ 6.6 (s, 1H), 7.4-8.0 (m, 9H), 8.2 (s, 1H).

Example 3

This illustrates the fluorogenic combination of phenylacetylene and 7-diethylamino-3-azidocoumarin to form 7-diethylamino-3-(4-phenyl-[1,2,3]triazol-1-yl)-chromen-2-one in an embodiment of the present method.

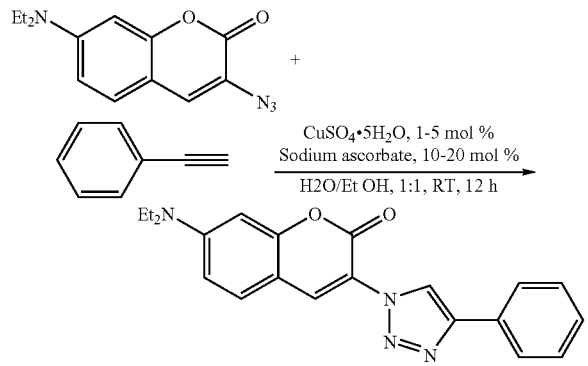

In a mixture of phenylacetylene (18 mg, 0.17 mmol) and 7-diethylamino-3-azidocoumarin (45 mg, 0.17 mmol) in water and ethyl alcohol (v/v=1:1, 5 mL), sodium ascorbate (34 μL, 0.034 mmol) of freshly prepared 1 M solution in water was added, followed by the addition of copper (II) sulfate pentahydrate 7.5% in water (28 μL, 0.0085 mmol). The heterogeneous mixture was stirred vigorously overnight in the dark at room temperature. TLC analysis indicated complete consumption of the reactants in 12 h. The ethanol was removed and the residue was diluted with water (5 ml), cooled in ice, and then the precipitate was collected by filtration. After washing the precipitate with cold water (10 ml), it was dried under vacuum to afford 53 mg of pure product as a yellow powder (84%); mp 242-244° C.; ¹H NMR (CDCl₃, 300 MHz) δ 1.26 (t, J=6.94 Hz, 6H), 3.48 (q, J=7.13 Hz, 4H), 6.50 (s, 1H), 6.70 (d, J=8.93 Hz, 1H), 7.4-7.6 (m, 4H), 7.9 (d, J=6.29 Hz, 1H), 8.5 (s, 1H), 8.8 (s, 1H). HRMS m/e calculated for (M+H)⁺ C₂₁H₂₀N₄O₂ 361.1663; found 361.1664.

Example 4

This example illustrates the fluorogenic conjugation of 7-diethylamino-3-azidocoumarin and phenylacetylene to form 7-diethylamino-3-(4-phenyl-[1,2,3]triazol-1-yl)-chromen-2-one.

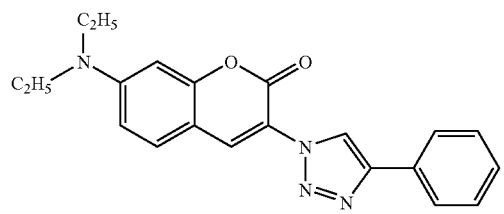

In a mixture of phenylacetylene (18 mg, 0.17 mmol) and 7-diethylamino-3-azidocoumarin (45 mg, 0.17 mmol) in water and ethyl alcohol (v/v=1:1, 5 ml), sodium scorbate (34 μl, 0.034 mmol) of freshly prepared 1 M solution in water was added, followed by the addition of copper (II) sulfate pentahydrate 7.5% in water (28 μl, 0.0085 mmol). The heterogeneous mixture was stirred vigorously overnight in the dark at room temperature. TLC analysis indicated complete consumption of the reactants in 12 h. The ethanol was removed and the residue was diluted with water (5 ml.), cooled in ice, and then the precipitate was collected by filtration. After washing the precipitate with cold water (10 ml), it was dried under vacuum to afford 53 mg of pure product as a yellow powder (84% yield); mp 242-244° C., ¹H NMR (CDCl₃, 300 MHz): δ 1.26 (t, J=6.94 Hz, 6H), 3.48 (q, J=7.13 Hz, 4H), 6.50 (s, 1H), 6.70 (d, J=8.93 Hz, 1H), 7.4-7.6 (m, 4H), 7.9 (d, J=6.29 Hz, 1H), 8.5 (s, 1H), 8.8 (s, 1H). HRMS m/e calculated for (M+H)⁺ C₂₁H₂₀N₄O₂ 361.1663; found 361.1664.

Examples 5-34

These examples show fluorogenic linkage complexes produced from combinations of the linkage compounds of Table 1 and Table 2.

| Example | Code | Structure | Analysis |
|---------|------|-----------|----------|
| 5 | A1 | 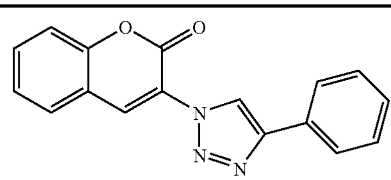 | Mp = 199-201° C.; ¹H NMR (CDCl₃, 300 MHz) δ 7.3-7.8 (m, 9H), 8.8 (s, 1H), 9.2 (s, 1 H); HRMS m/e calculated for MH⁺ C₁₇H₁₁N₃O₂ 290.0922, found 290.0930. |

| Example | Code | Analysis |
|---|---|---|
| 6 | A2 | Mp 220-222° C.; ¹H NMR (DMSO-d₆, 300 MHz) δ 2.39 (s, 3H), 7.31 (d, J = 8.88 Hz, 2H), 7.54 (m, 2H), 7.78 (t, 1H), 7.91 (d, J = 10.15 Hz, 2H), 7.98 (d, J = 6.34 Hz, 1H), 8.73 (s, 1H), 8.93 (s, 1H); HRMS m/e calculated for M⁺ $C_{18}H_{13}N_3O_2$ 303.1001, found 304.1008. |
| 7 | A3 | Mp >250° C.; ¹H NMR (CDCl₃, 300 MHz,) δ 7.44-7.74 (m, 6H), 8.07 (d, J = 8.05 Hz, 2H), 8.70 (s, 1H), 9.03 (s, 1H); HRMS m/e calculated for MH⁺ $C_{19}H_{10}F_3N_3O_2$ 358.0809, found 358.0803. |
| 8 | A7 | Mp = 186-188° C.; ¹H NMR (CDCl₃, 300 MHz): δ 0.88 (t, J = 6.89 Hz, 3H), 1.33 (m, 4H), 1.56 (m, 2H), 2.64 (t, J = 7.80 Hz, 2H), 7.30-7.47 (m, 3H), 7.69 (m, 3H), 7.82 (d, J = 8.21 Hz, 2H), 8.67 (s, 1H), 8.88 (s, 1H). HRMS m/e calculated for MH⁺ $C_{22}H_{21}N_3O_2$ 360.1711, found 360.1712. |
| 9 | A18 | Mp = 180-185° C.; ¹H NMR (DMSO-d₆, 300 MHz) δ 7.61-7.98 (m, 11H), 8.81 (s, 1H), 9.10 (s, 1H); EI-HRMS m/e calculated for M⁺ $C_{21}H_{13}N_3O_2$ 340.1086, found 340.1098. |
| 10 | B1 | Mp >250° C.; ¹H NMR (DMSO-d₆, 300 MHz) δ 6.87 (m, 2H), 6.89 (m, 1H), 7.38 (m, 1H), 7.44 (t, J = 6.77 Hz, 2H), 7.52 (d, J = 8.27 Hz, 1H), 8.63 (s, 1H), 8.98 (s, 1H). HRMS m/e calculated for M⁺ $C_{17}H_{11}N_3O_3$ 306.0878, found 376.0892. |
| 11 | B2 | Mp >250° C.; ¹H NMR (DMSO-d₆, 300 MHz) δ 2.33 (s, 3H), 6.89 (m, 2H), 7.28 (d, J = 9.75 Hz, 2H), 7.75 (d, J = 7.80 Hz, 1H), 7.82 (d, J = 5.85 Hz, 2H), 8.63 (s, 1H), 8.92 (s, 1H), 10.93 (s, 1H). HRMS m/e calculated for MH⁺ $C_{18}H_{13}N_3O_3$ 320.1035, found 320.1044. |
| 12 | B7 | Mp 209-211° C.; ¹H NMR (DMSO-d₆, 300 MHz) δ 0.85 (t, J = 5.11 Hz, 3H), 1.26 (m, 4H), 1.56 (p, J = 7.15 Hz, 2H), 2.59 (t, J = 8.17 Hz, 2H), 6.92 (m, 2H), 7.29 (d, J = 6.54 Hz, 2H), 7.76 (d, J = 10.46 Hz, 1H), 7.83 (d, J = 7.85 Hz, 3H), 8.63 (s, 1H), 8.92 (s, 1H). EI-HRMS m/e calculated for M⁺ $C_{22}H_{21}N_3O_3$ 376.1661, found 376.1664. |
| 13 | B11 | Mp >250° C.; ¹H NMR (DMSO-d₆, 300 MHz) δ 7.39 (m, 5H), 8.18 (t, J = 7.94 Hz, 2H), 8.65 (s, 1H), 8.81 (d, J = 3.49 Hz, 1H). HRMS m/e calculated for MH⁺ $C_{17}H_{10}FN_3O_3$ 324.0784, found 324.0783. |

-continued

| Example | Code | Structure | Analysis |
|---|---|---|---|
| 14 | B23 | 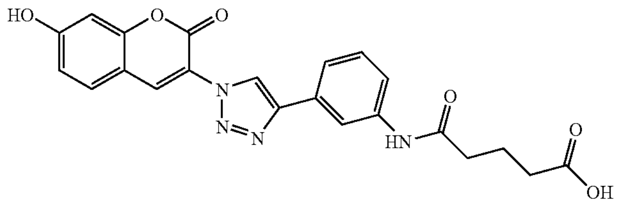 | Mp 212-218° C.; $^1$H NMR (DMSO-d$_6$, 300 MHz) δ 1.82 (p, J = 8.37 Hz, 2H), 2.26 (t, J = 7.53 Hz, 2H), 2.34 (t, J = 6.90 Hz, 2H), 6.92 (m, 2H), 7.38 (t, J = 7.44 Hz, 1H), 7.57 (t, J = 8.68 Hz, 2H), 7.64 (d, J = 8.68 Hz, 1H), 8.21 (s, 1H), 8.65 (s, 1H), 8.92 (s, 1H), 10.0 (s, 1H), 10.91 (s, 1H); EI-HRMS m/e calculated for MS$^+$ C$_{22}$H$_{18}$N$_4$O$_6$ 435.1304, found 435.1299. |
| 15 | C3 | 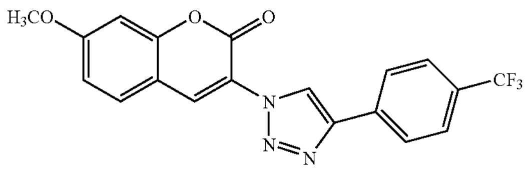 | $^1$H NMR (DMSO-d$_6$, 300 MHz) δ 3.90 (s, 3H), 7.09(dd, J = 8.9, 2.8 Hz, 1H), 7.19 (d, J = 2.2 Hz, 1H), 7.85 (m, 3H), 8.19 (d, J = 8.4 Hz, 2H), 8.74 (s, 1H), 9.22 (s, 1H). |
| 16 | D6 | 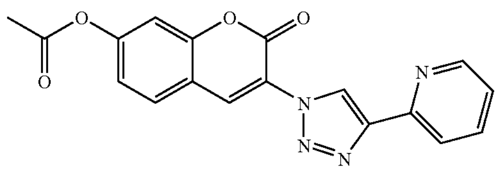 | Mp >250° C.; $^1$H NMR (DMSO-d$_6$, 300 MHz) δ 2.32 (s, 3H), 7.28 (d, J = 6.87 Hz, 2H), 7.46 (s, 2H), 8.00 (d, J = 8.80 Hz, 3H), 8.87 (s, 2H). HRMS m/e calculated for MH$^+$ C$_{18}$H$_{12}$N$_4$O$_4$ 349.0937, found 349.0937. |
| 17 | D13 | 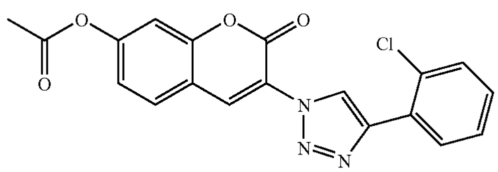 | Mp decomp. at 205° C.; $^1$H NMR (DMSO-d$_6$, 400 MHz) δ 2.31 (s, 1H), 7.28 (d, J = 7.8 Hz, 2H), 7.47 (m, 3H), 7.61 (d, J = 7.97 Hz, 2H), 8.12 (d, J = 8.44 Hz, 1H), 8.78 (s, 1H), 9.09 (s, 1H). HRMS m/e calculated for MH$^+$ C$_{18}$H$_{12}$ClN$_3$O$_4$ 382.0594, found 382.0591. |
| 18 | E7 | 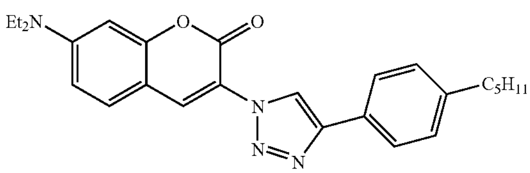 | Mp = 173-175° C.; $^1$H NMR (CDCl$_3$, 300 MHz): δ 0.90 (t, J = 6.27 Hz, 3H), 1.22 (t, J = 7.33 Hz, 6H), 1.32 (m, 4H), 1.55 (m, 2H), 2.64 (t, J = 8.02 Hz, 2H), 3.47 (q, J = 7.46 Hz, 4H), 6.70 (d, J = 6.7 Hz, 1H), 6.56 (d, J = 6.56 Hz, 1H), 7.41 (d, J = 9.25 Hz, 2H), 7.81 (d, J = 8.38 Hz, 3H), 8.45 (s, 1H), 8.78 (s, 1H). HRMS m/e calculated for MH$^+$ C$_{26}$H$_{30}$N$_4$O$_2$ 431.2451, found 431.2447 |
| 19 | E8 | 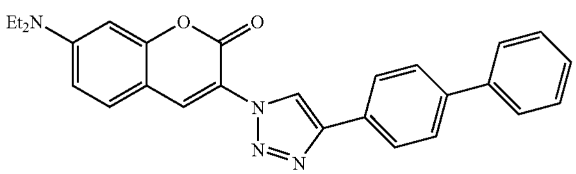 | Mp = 203-205° C.; $^1$H NMR (CDCl$_3$, 300 MHz): δ 1.25 (t, J = 7.25 Hz, 6H), 3.48 (q, J = 7.21 Hz, 4H), 6.57 (s, 1H), 6.70 (d, J = 6.66 Hz, 1H), 7.36-7.48 (m, 4H), 7.64-7.71 (m, 4H), 8.01 (d, J = 8.27 Hz, 1H), 8.48 (s, 1H), 8.86 (s, 1H). HRMS m/e calculated for MH$^+$ C$_{27}$H$_{24}$N$_4$O$_2$ 437.1981, found 437.1977. |
| 20 | E10 | 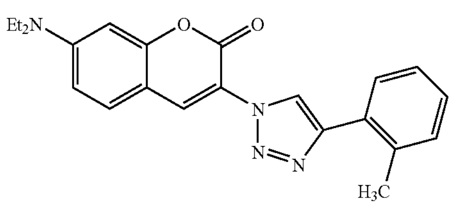 | Mp = 165-167° C.; $^1$H NMR (CDCl$_3$, 300 MHz): δ 1.25 (t, J = 6.93 Hz, 6H), 2.54 (s, 3H), 3.47 (q, J = 7.26 Hz, 4H), 6.68 (s, 1H), 6.71 (m, 1H), 7.29-7.40 (m, 5H), 7.80 (m, 1H), 8.46 (s, 1H), 8.50 (s, 1H); HRMS m/e calculated for MH$^+$ C$_{22}$H$_{22}$N$_4$O$_2$ 375.1824, found 375.1821. |
| 21 | E14 | 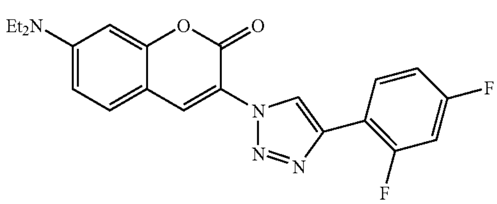 | Mp = 204-206° C.; $^1$H NMR (CDCl$_3$, 300 MHz): δ 1.25 (t, J = 7.38 Hz, 6H), 3.47 (q, J = 7.15 Hz, 4H), 6.57 (s, 1H), 6.70 (m, J = 6.58 Hz, 1H), 6.71-7.01 (m, 2H), 7.33-7.44 (m, 3H), 8.30 (m, 1H), 8.28 (s, 1H) 8.85 (s, 1H); HRMS m/e calculated for MH$^+$ C$_{21}$H$_{18}$N$_4$O$_2$F$_2$ 397.1482, found 397.1476. |

| Example | Code | Structure | Analysis |
|---|---|---|---|
| 22 | E23 | 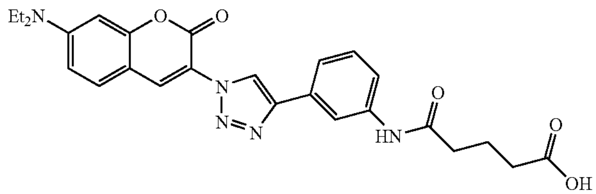 | Mp 223-225° C.; ¹H NMR (DMSO-d₆, 300 MHz) δ 1.56 (t, J = 7.66 Hz, 6H), 2.81 (p, J = 8.36 Hz, 2H), 2.30 (t, J = 7.16 Hz, 2H), 2.39 (t, J = 8.36 Hz, 2H), 3.47 (q, J = 7.91 Hz, 4H), 6.68 (s, 1H), 6.84 (d, J = 7.79 Hz, 1H), 7.38 (m, 1H), 7.61 (m, 2H), 8.12 (s, 1H), 8.54 (s, 1H), 8.87 (s, 1H), 10.0 (s, 1H), 12.1 (s, 1H); EI-HRMS m/e calculated for MS⁺ C₂₆H₂₇N₅O₅ 490.2090, found 490.2095. |
| 23 | F1 | 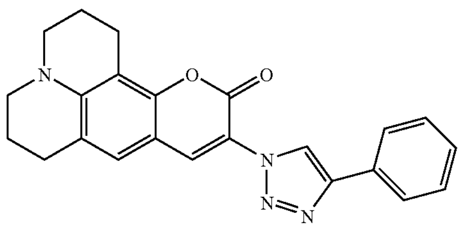 | mp >250° C.; ¹H NMR (CDCl₃, 300 MHz) δ 1.97-2.03 (m, 4H), 2.80-2.96 (m, 4H), 3.35 (m, 4H), 7.02 (s, 1H), 7.34-7.51 (m, 3H), 7.91 (d, J = 8.16 Hz, 2H), 8.37 (s, 1H), 8.82 (s, 1H); HRMS m/e calculated for MH⁺ C₂₃H₂₀N₄O₂ 385.1660, found 385.1664. |
| 24 | F7 | 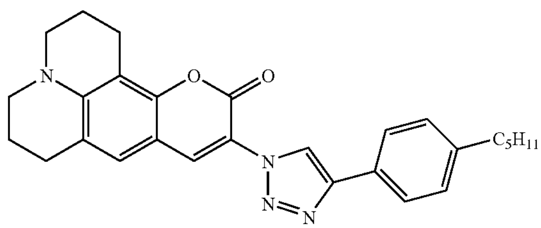 | Mp = 158-160° C.; ¹H NMR (CDCl₃, 300 MHz) δ 0.85 (t, J = 7.25 Hz, 3H), 1.26-1.90 (m, 8H), 1.94 (m, 2H), 2.57-2.89 (m, 6H), 3.28 (m, 4H), 7.07 (s, 1H), 7.20 (d, 2H), 7.78 (d, J = 8.16 Hz, 2H), 8.30 (s, 1H), 8.72 (s, 1H); HRMS m/e calculated for MH⁺ C₂₈H₃₀N₄O₂ 455.2447, found 455.2447. |
| 25 | F15 | 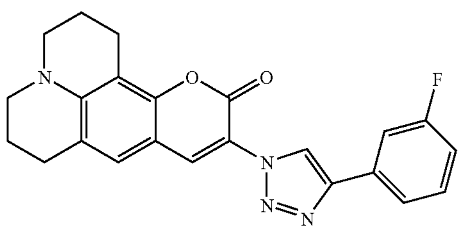 | Mp = 203-205° C.; ¹H NMR (CDCl₃, 300 MHz) δ 1.97-2.03 (m, 4H), 2.80-2.96 (m, 4H), 2.39 (s, 3H), 3.35 (m, 4H), 7.01 (s, 1H), 7.25-7.33 (m, 2H), 7.82 (d, J = 8.17 Hz, 2H), 8.36 (s, 1H), 8.77 (s, 1H); HRMS m/e calculated for MH⁺ C₂₃H₁₉FN₄O₂ 403.1574, found 403.1570. |
| 26 | F23 | 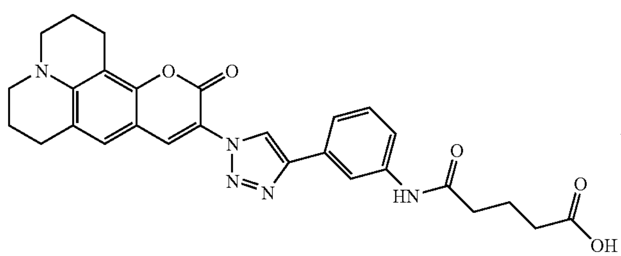 | Mp 177-178° C.; ¹H NMR (DMSO-d₆, 300 MHz) δ 1.87 (m, 7H), 2.23-2.41 (m, 5H), 2.76 (m, 5H), 7.28 (s, 1H), 7.38 (t, J = 5.7 Hz, 1H), 7.59 (m, 3H), 8.18 (s, 1H), 8.20 (s, 1H), 8.84 (s, 1H), 10.0 (s, 1H); EI-HRMS m/e calculated for M⁺ C₂₈H₂₇N₅O₅ 514.2090, found 514.2076. |
| 27 | G7 | 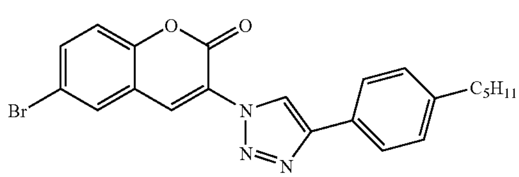 | ¹H NMR (CDCl₃, 300 MHz) δ 0.88 (t, J = 6.7 Hz, 3H), 1.32 (m, 4H), 1.64 (m, 2H), 2.63 (t, J = 7.6 Hz, 2H), 7.26 (d, J = 8.0 Hz, 2H), 7.33 (d, J = 9.0 Hz, 1H), 7.71 (dd, J = 8.7, 2.3 Hz, 1H), 7.82 (m, 3H), 8.59 (s, 1H), 8.89 (s, 1H). |
| 28 | H2 | 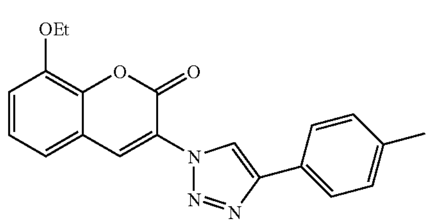 | ¹H NMR (CDCl₃, 300 MHz) δ 2.38 (s, 1H), 4.18 (q, J = 7.3 Hz, 2H), 4.23 (t, J = 7.0 Hz, 3H), 7.24 (m, 5H), 7.80 (d, J = 8.2 Hz, 2H), 8.62 (s, 1H), 8.89 (s, 1H). |

-continued

| Example | Code | Structure | Analysis |
|---|---|---|---|
| 29 | I1 | 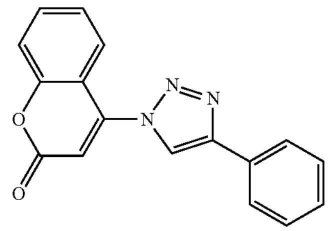 | Mp = 166-168° C.; $^1$H NMR (CDCl$_3$, 300 MHz) δ 6.6 (s, 1H), 7.4-8.0 (m, 9H), 8.2 (s, 1H); HRMS m/e calculated for MH$^+$ C$_{17}$H$_{11}$N$_3$O$_2$ 290.0934, found 290.0930. |
| 30 | I2 | 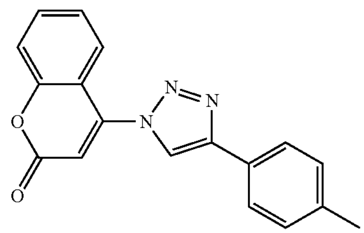 | Mp = 181-183° C.; $^1$H NMR (CDCl$_3$, 300 MHz) δ 2.40 (s, 3H), 7.29-7.83 (m, 8H), 8.66 (s, 1H), 8.88 (s, 1H); HRMS m/e calculated for MH$^+$ C$_{18}$H$_{13}$N$_3$O$_2$ 304.1090, found 304.1086. |
| 31 | I4 | 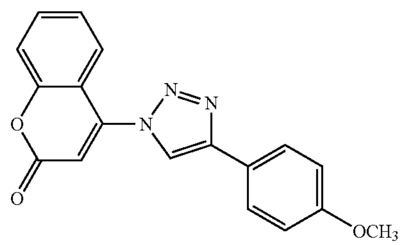 | Mp = 183-185° C.; $^1$H NMR (CDCl$_3$, 300 MHz) δ 3.87 (s, 3H), 6.61 (s, 1H), 7.00 (d, J = 8.58 Hz, 2H), 7.30-7.50 (m, 2H), 7.84 (d, J = 8.83 Hz, 1H), 7.86 (m, 1H), 7.90 (d, J = 8.8 Hz, 2H), 8.11 (s, 1H); HRMS m/e calculated for MH$^+$ C$_{18}$H$_{13}$N$_3$O$_3$ 320.1041, found 320.1035. |
| 32 | I13 | 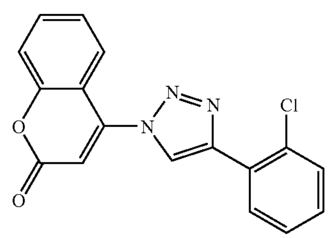 | Mp = 156-158° C.; $^1$H NMR (CDCl$_3$, 300 MHz) δ 6.67 (s, 1H), 7.30-7.70 (m, 6H), 8.00 (d, J = 6.71 Hz, 1H), 8.35 (d, J = 6.03 Hz, 1H), 8.66 (s, 1H). HRMS m/e calculated for MH$^+$ C$_{17}$H$_{10}$ClN$_3$O$_2$ 324.0547, found 324.0540. |
| 33 | I15 | 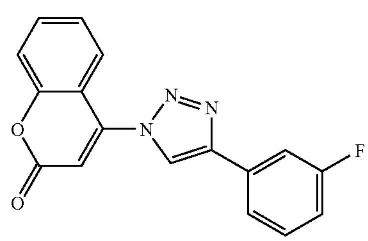 | Mp = 177-179° C.; $^1$H NMR (DMSO-d$_6$, 300 MHz,) δ 6.99 (S, 1H), 7.24 (m, 1H), 7.40-7.60 (m, 3H), 7.75-7.89 (m, 3H), 7.94 (d, J = 7.21 Hz, 1H), 9.35 (s, 1H); HRMS m/e calculated for MH$^+$ C$_{17}$H$_{10}$FN$_3$O$_2$ 308.0843, found 308.0835 |
| 34 | J23 | 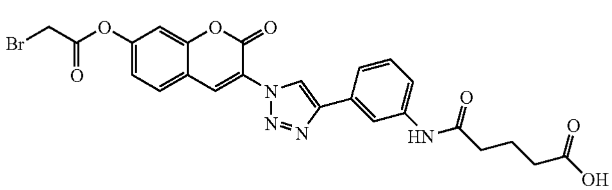 | Mp decomp. at 180° C.; $^1$H NMR (DMSO-d$_6$, 300 MHz) δ 1.18 (p, J = 7.87 Hz, 2H), 2.06 (s, 2H), 2.30 (t, J = 8.99 Hz, 2H), 2.37 (t, J = 5.62 Hz, 2H), 7.17-7.72 (m, 5H), 8.02 (d, J = 7.62 Hz, 1H), 8.24 (s, 1H), 8.80 (s, 1H), 8.98 (s, 1H), 10.0 (s, 1H), 12.1 (s, 1H). EI-HRMS m/e calculated for M$^+$ C$_{24}$H$_{19}$BrN$_4$O$_6$ 555.0515, found 555.0499. |

Example 35

This example illustrates the use of a cyano-substituted coumarin and an azide as fluorogenic linkers to form a fluorescent linkage product.

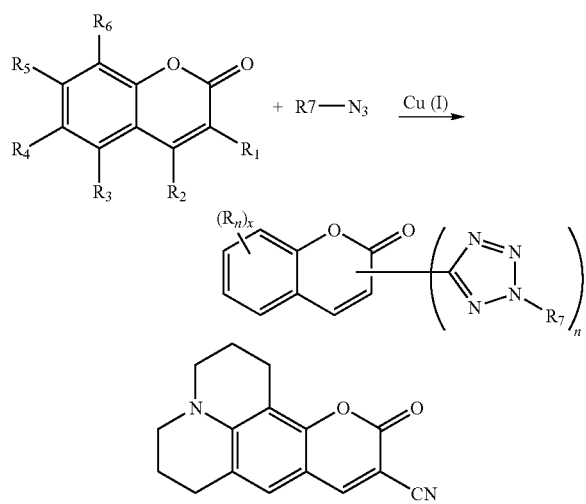

In the scheme shown above, one to six of $R_1$, $R_2$, $R_3$, $R_4$, $R_5$ and $R_6$ is ethynyl group(s), the rest will be hydrogen or any other chemically possible substituent, including, but not limited to hydroxyl, alkyl, alkenyl, alkynyl, halo, carboxyl, alkoxyl, amino, hydroxyalkyl, any of which may be substituted or unsubstituted, as well as possible ring connections, as shown in the structure below the reaction. $R_7$ can be any possible chemical substituent.

Example 36

This example illustrates the formation of a fluorogenic linkage complex from a first linkage compound that is a halide and a second linkage compound that is a tertiary alkyne in the presence of sodium azide.

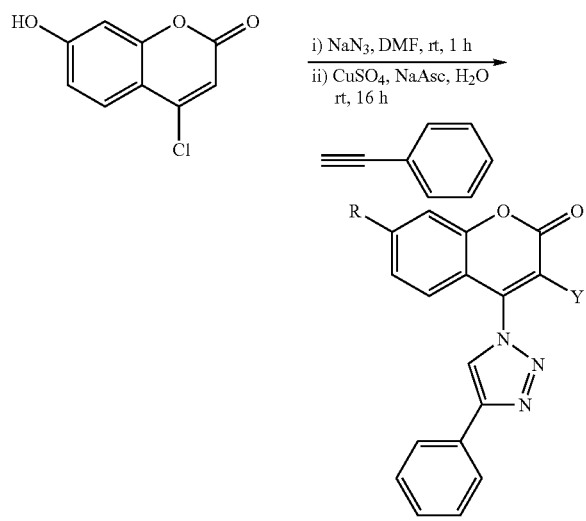

In this scheme, 4-chloro-7-hydroxycoumarin (78.4 mg, 0.4 mmol) and sodium azide (31 mg, 0.48 mmol) were mixed in DMF (1.5 mL) and stirred for 1 h. Then, $CuSO_4$ (12.8 mg, 0.08 mmol), sodium ascorbate (31.7 mg, 0.16 mmol) and phenylacetylene (40.8 mg, 0.4 mmol) were added together with water (0.6 mL). The mixture was stirred at room temperature overnight until the reaction was completed. The crude reaction mixture was poured into ice water (15 mL). The precipitate was isolated by filtration, washed with dilute $NH_4OH$ and dried under vacuum to yield the product as off-white solid (78 mg, 64%).

In other tests, using the same conditions, but differently substituted coumarin reactants, it was found that successful fluorescent products were produced with substituted coumarins having either bromo or chloro at the 4-position, and having either hydrogen, amino, nitro, carboxyl, halo, or alkyl substituents at the 7-position.

Example 37

This example illustrates the formation of a fluorogenic linkage complex from a first linkage compound that is a halide and a second linkage compound that is a tertiary alkyne in the presence of sodium azide.

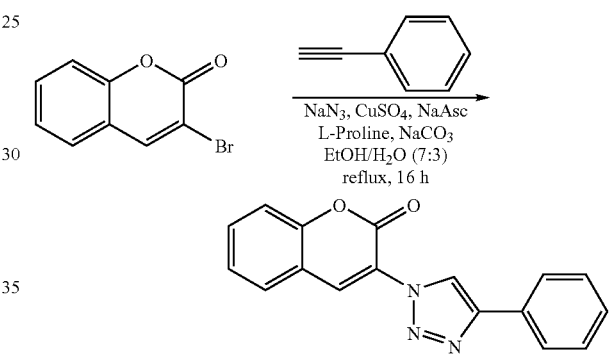

In this scheme, 3-bromocoumarin (46.0 mg, 0.25 mmol) was mixed with sodium azide (19.5 mg, 0.3 mmol), $CuSO_4$ (9.8 mg, 0.05 mmol), sodium ascorbate (19.8 mg, 0.1 mmol), L-proline (11.5 mg, 0.1 mmol), $Na_2CO_3$ (10.6 mg, 0.1 mmol), and phenylacetylene (25.5 mg, 0.25 mmol) in ethanol/water (7:3, 5 mL). The mixture was stirred overnight at 90° C. Upon completion (monitored by TLC), the crude reaction mixture was poured into ice water (15 mL). The precipitate was isolated by filtration, washed with dilute $NH_4OH$ solution and dried under vacuum to yield the final product as white solid (50 mg, 69%).

Example 38

This example illustrates the procedure of bioconjugation.

Figure 7:
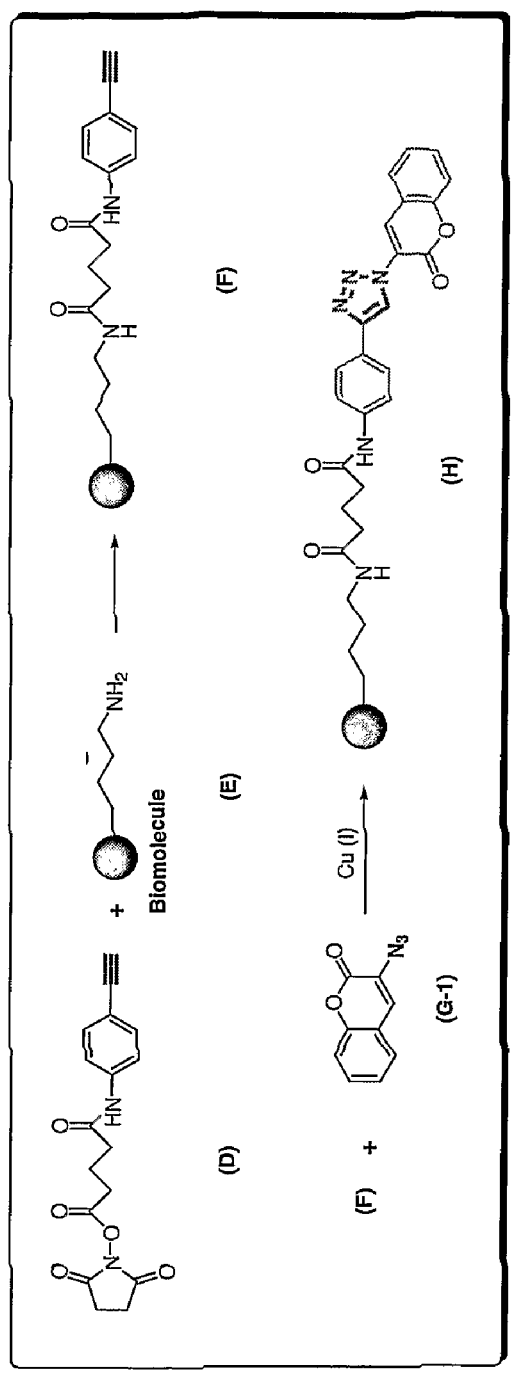
FIG. 7 illustrates an example of bioconjugation using an embodiment of the present method wherein a tertiary alkyne is linked with a biomolecule having an amino functional group to form a biomolecule bound to a substituent group having an alkyne, which can be reacted with a compound having an azido group to yield a fluorescent conjugated linkage complex.

As illustrated in FIG. 7, wild type cowpea mosaic virus (10 mg) was mixed with compound "D" (1 mg) in a mixture of potassium phosphate buffer (0.1 M, pH=7.0, 9 mL) and DMF (1 mL). The mixture was incubated at 4° C. for 24 hours before purified with ultracentrifugation to afford the compound designated as "F". 3-Azidocoumarin ("G-1") and "F" were mixed with copper sulfate, sodium ascorbate and some azacyclic ligands in a mixture of potassium phosphate buffer (0.1 M, pH=7.0, 9 mL) and DMF (1 mL), to make the final concentration of Cu and sodium ascorbate to be 1 mM. After 24 hours incubation at 4° C., the mixture is analyzed directly by fluoriphotometer. Upon irradiation at 340 nm, a strong fluorescent emission at 478 nm can be detected.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions by those of ordinary skill in the art without departing from the scope of the invention, it is intended that all matter contained in the above description and shown in the accompanying drawings shall be interpreted as illustrative and not in a limiting sense. In addition it should be understood that aspects of the various embodiments may be interchanged both in whole or in part.

What is claimed is:

1. A method of forming a linkage complex having a fluorescent signal, the method comprising:
reacting a fluorophore with a linkage compound to form a linkage complex having a fluorescent signal that is different than a fluorescent signal of the fluorophore; wherein the fluorophore comprises coumarin substituted at position 3 or 4 with at least one azide group (—$N_3$); and wherein the linkage compound has the structure

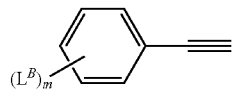

where: m is 1 and $L^B$ comprises a linking group bonded to a biomolecule.

2. The method according to claim 1, wherein the linkage complex comprises a triazole.

3. The method according to claim 1, wherein the linkage complex comprises 1,2,3-triazole.

4. The method according to claim 1, wherein the fluorophore comprises a coumarin compound having the structure:

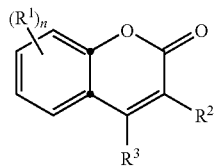

where:
n is an integer from 0 to 4;
each $R^1$ is the same or different and is any chemically possible substituent group, optionally two or more $R^1$ groups join to form one or more substituted or unsubstituted rings; and
at least one of $R^2$ and $R^3$ is —$N_3$, and the other is any $R^1$ group.

5. The method according to claim 4, wherein:
each $R^1$ is the same or different and is selected from hydrogen, hydroxyl, alkyl, alkenyl, alkynyl, halo, carboxyl, carbonyl, alkyloxyl, alkoxyl, alkoxyalkyl, amino, alkylamino, azido, hydroxyalkyl, sulfonyl, sulfinyl, phospho, phosphino, or optionally two or more $R^1$ groups join to form one or more substituted or unsubstituted rings.

6. The method according to claim 4, wherein $R^2$ comprises —$N_3$, and $R^3$ comprises any $R^1$ group.

7. The method according to claim 1, wherein the fluorophore comprises 3-azidocoumarin.

8. The method according to claim 1, wherein the fluorophore comprises 3-azido-7-dimethylaminocoumarin.

9. The method according to claim 1, wherein the fluorophore comprises 3-azido-7-hydroxycoumarin.

10. The method according to claim 1, wherein the fluorophore comprises 3-azido-7-methoxycoumarin.

11. The method according to claim 1, wherein the fluorophore comprises 7-acetic-3-azidocoumarin.

12. The method according to claim 1, wherein the fluorophore comprises 3-azido-7-diethylaminocoumarin.

13. The method according to claim 1, wherein the fluorophore comprises 3-azido-6-bromocoumarin.

14. The method according to claim 1, wherein the fluorophore comprises 4-azidocoumarin.

15. The method according to claim 1, wherein the fluorophore is chemically bonded to a second biomaterial.

16. The method according to claim 15, wherein the fluorophore is chemically bonded to the biomaterial according to the structure:

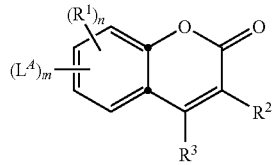

where:
n is an integer from 0 to 3;
m is 1;
each $R^1$ is the same or different and is any chemically possible substituent group, optionally two or more $R^1$ groups join to form one or more substituted or unsubstituted rings;
at least one of $R^2$ and $R^3$ is —$N_3$ and the other is any $R^1$ group; and
$L^A$ is a linking group chemically bonded to the second biomaterial.

17. The method according to claim 16, wherein $L^A$ is an organic substituent group having at least one reactive group that is selected from carboxylic acid esters, sulfonyl halide, acyl halide, aldehydes, reactive ketones, aromatic halides, bromoacetamides, idoacetamides, maleimides, disulfides, hydroxyl, amines, diazonium compounds, active alkylating reagents, active acylating reagents, or diketones.

18. The method according to claim 16, wherein $L^A$ is an organic substituent group that is selected from branched or unbranched $C_1$-$C_{12}$ alky, $C_1$-$C_{12}$ alkenyl, $C_1$-$C_{12}$ alkynyl, or aryl, heteroaryl, or heterocyclyl, and which has at least one substituent reactive group that is selected from carboxylic acid esters, sulfonyl halide, acyl halide, aldehydes, reactive ketones, aromatic halides, bromoacetamides, idoacetamides, maleimides, disulfides, hydroxyl, amines, diazonium compounds, active alkylating reagents, active acylating reagents, or diketones.

19. The method according to claim 15, wherein the second biomaterial is selected from small molecules, drugs, ligands, catalysts, peptides, proteins, nucleic acids, oligonucleotides, saccharides, viruses, cells, organic polymers, inorganic polymers, nanoparticles, or solid surfaces.

20. The method according to claim 1, wherein the biomaterial is selected from small molecules, drugs, ligands, catalysts, peptides, proteins, nucleic acids, oligonucleotides, saccharides, viruses, cells, organic polymers, inorganic polymers, nanoparticles, or solid surfaces.

21. The method according to claim 1 further comprising measuring the fluorescent signal of the linkage complex.

22. A kit for forming a linkage complex having a fluorescent signal, the kit comprising
a fluorophore comprising coumarin substituted at position 3 or 4 with at least one azide group ($-N_3$); and
a linkage compound, wherein the linkage compound has the structure

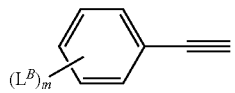

where: m is 1 and $L^B$ comprises a linking group bonded to a biomolecule.

23. The kit according to claim 22, wherein the fluorophore comprises a coumarin compound having the structure:

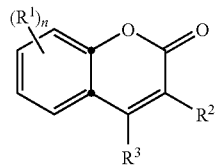

where:
n is an integer from 0 to 4;
each $R^1$ is the same or different and is any chemically possible substituent group, optionally two or more $R^1$ groups join to form one or more substituted or unsubstituted rings; and
at least one of $R^2$ and $R^3$ is $-N_3$, and the other is any $R^1$ group.

24. The kit according to claim 23, wherein:
each $R^1$ is the same or different and is selected from hydrogen, hydroxyl, alkyl, alkenyl, alkynyl, halo, carboxyl, carbonyl, alkyloxyl, alkoxyl, alkoxyalkyl, amino, alkylamino, azido, hydroxyalkyl, sulfonyl, sulfinyl, phospho, phosphino, or optionally two or more $R^1$ groups join to form one or more substituted or unsubstituted rings.

25. The kit according to claim 23, wherein $R^2$ comprises $-N_3$, and $R^3$ comprises any $R^1$ group.

26. The kit according to claim 22, wherein the fluorophore comprises 3-azidocoumarin.

27. The kit according to claim 22, wherein the fluorophore comprises 3-azido-7-dimethylaminocoumarin.

28. The kit according to claim 22, wherein the fluorophore comprises 3-azido-7-hydroxycoumarin.

29. The kit according to claim 22, wherein the fluorophore comprises 3-azido-7-methoxycoumarin.

30. The kit according to claim 22, wherein the fluorophore comprises 7-acetic-3-azidocoumarin.

31. The kit according to claim 22, wherein the fluorophore comprises 3-azido-7-diethylaminocoumarin.

32. The kit according to claim 22, wherein the fluorophore comprises 3-azido-6-bromocoumarin.

33. The kit according to claim 22, wherein the fluorophore comprises 4-azidocoumarin.

34. The kit according to claim 22, wherein the fluorophore is chemically bonded to a biomaterial.

35. The kit according to claim 22, wherein the fluorophore is chemically bonded to a second biomaterial.

36. The kit according to claim 35, wherein the fluorophore comprises a compound having the structure:

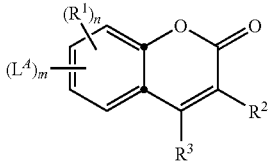

where:
n is an integer from 0 to 3;
m is 1;
each $R^1$ is the same or different and is any chemically possible substituent group, optionally two or more $R^1$ groups join to form one or more substituted or unsubstituted rings;
at least one of $R^2$ and $R^3$ is $-N_3$, and the other is any $R^1$ group; and
$L^A$ is a linking group chemically bonding the fluorophore to the second biomaterial.

37. The kit according to claim 35, wherein the second biomaterial is selected from small molecules, drugs, ligands, catalysts, peptides, proteins, nucleic acids, oligonucleotides, saccharides, viruses, cells, organic polymers, inorganic polymers, nanoparticles, or solid surfaces.

38. The kit according to claim 22, wherein the biomaterial is selected from small molecules, drugs, ligands, catalysts, peptides, proteins, nucleic acids, oligonucleotides, saccharides, viruses, cells, organic polymers, inorganic polymers, nanoparticles, or solid surfaces.

39. The kit according to claim 22 further comprising a catalyst, wherein the catalyst comprises copper(I).

40. The method according to claim 1 wherein reacting the fluorophore with the linkage compound to form the linkage complex is catalyzed with copper(I).

* * * * *